United States Patent [19]
Graneto et al.

[11] Patent Number: 6,143,892
[45] Date of Patent: Nov. 7, 2000

[54] PROCESS FOR MAKING 5-SUBSTITUTED PYRAZOLES

[75] Inventors: Matthew J. Graneto, Chesterfield; Michael L. Vazquez, Ballwin; Susan J. Hartmann, Kirkwood; Suzanne Metz, Chesterfield; John J. Talley, St. Louis; David L. Brown, Chesterfield, all of Mo.; Richard M. Weier, Lake Bluff, Ill.; Michael A. Stealey, Libertyville, Ill.; Xiaodong C. Xu, Gurnee, Ill.

[73] Assignee: G. D. Searle & Co., Chicago, Ill.

[21] Appl. No.: 09/442,971

[22] Filed: Nov. 18, 1999

Related U.S. Application Data

[60] Provisional application No. 60/109,177, Nov. 20, 1998.
[51] Int. Cl.$^7$ .................................................. C07D 401/14
[52] U.S. Cl. ............................ 544/364; 544/60; 544/295; 548/371.4
[58] Field of Search .......................... 548/371.4; 544/364

[56] References Cited

PUBLICATIONS

Katagiri, N.; Synthesis of Nucleosides and Related Compounds . . . ; Chem. Pharm. Bull. 1990, 12, 3242–3248.

Okajima, N.; Synthesis of Tiocarbonyl and Heterocyclic Compounds from 2–Methylene–1; . . . ; J. Heterocyclic Chem. 1990, 27, 567–574.

Huang, Z. N.; Synthesis of 5–Mercaptoalkylthiopyrazolyl . . . , Synth. Commun. 1996, 26, 3115–3120.

Huang, Z. H.; Synthesis of 5–Mercaptoalkylamino– and . . . Heterocycles 1995, 41, 1653–1658.

*Primary Examiner*—Robert W. Ramsuer
*Attorney, Agent, or Firm*—Alan L. Scrivner

[57] ABSTRACT

This invention relates to a novel process of preparing selected 5-substituted pyrazoles useful as p38 kinase and COX-2 inhibitors.

5 Claims, No Drawings

ID

PROCESS FOR MAKING 5-SUBSTITUTED PYRAZOLES

This application claims priority to U.S. Provisional Application No. 60/109,177 filed Nov. 20, 1998.

FIELD OF THE INVENTION

This invention relates to the preparation of selected substituted heterocycles that are useful for the treatment of inflammatory diseases. In particular, the application discloses a method for the preparation of a number of substituted heterocycles that are p38 kinase and COX-2 inhibitors. The heterocycles described herein may be useful for the treatment of other disease states.

RELATED ART

Dithietanes have previously been prepared from selected 1,3-dicarbonyl compounds. These so-called active methylene compounds include esters of malonic acid, beta-keto esters, and 1,3-diketones [(1) Katagiri, N.; Ise, S.; Watanabe, N.; Kaneko, C., *Chem. Pharm. Bull.* 1990, 12, 3242–3248. (2) Okajima, N.; Okada, Y., *J. Heterocyclic Chem.* 1990, 27, 567–57.] Selected dithioles derived from esters of malonic acid have been described as inhibitors of cancer metastasis. [Onaka, S.; Gokou, S. Japanese Patent Application JP 10212239 1998. Certain (1,2,4-triazolyl)ketene S,S-acetals have been previously reported to react with hydrazine to afford pyrazolyl-1,2,4-triazoles. [Huang Z. N.; Li, Z. M., *Synth. Commun.* 1996, 26, 3115–3120.] Condensation of selected cyclic alpha-oxo-alpha-(1,2,4-triazol-1-yl)ketene N,S-acetals with hydrazine afforded 5-mercaptoalkylamino- and 5-anilinoalkylthiopyrazolyl-1,2,4-triazoles. [(1) Huang, Z. N.; Li, Z. M., *Heterocycles* 1995, 41, 1653–1658.] Historically, 3-amino-pyrazoles have been prepared by a sulfur extrusion rearrangement from 6H-1,3,4-thiadiazine derivatives in the presence of base. [(1) Beyer, H.; Honeck, H.; Reichelt, L., *Justus Liebigs Ann. Chem.* 1970, 741, 45. (2) Schmidt, R. R.; Huth, H., *Tetrahedron Lett.*, 1975, 33. (3) Pfeiffer, W. D.; Dilk, E.; Bulka, E., *Synthesis*, 1977, 196–198.1 This experimental protocol normally works adequately for the preparation of simple 3-amino-4-pyrazoles. The 6H-1,3,4-thiadiazine derivatives are in turn prepared by the condensation of alpha-chloroketones with thiosemicarbazides. This in turn necessitates preparing both the requisite alpha-chloroketone and thiosemicarbazide. In general, the aforementioned methodology was not useful for the preparation of the anti-inflammatory pyrazoles of the present invention. The known literature methods for the preparation of pyrazoles described above suffered from poor chemical yields and often gave mixtures of products that necessitated a careful chromatographic separation. In a number of instances, no desired pyrazole at all could be obtained using the methods disclosed in the literature. The present method has the advantage of being more direct (fewer steps) and provides the desired pyrazoles in significantly higher yield an I with higher purity. In addition, the present method has the added advantage that it does not rely on the preparation of unstable alpha-chloroketones. Frequently the alpha-chloroketones suffered de-chlorination upon treatment with thioseniicarbazides.

SUMMARY OF THE INVENTION

This invention encompasses a process for the preparation of selected substituted pyrazole derivatives of the Formula A and B useful for the treatment of inflammatory diseases, wherein Y is $SR_6$, $NR_4R_5$, or $OR_6$.

A

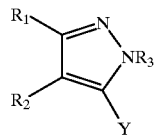

B

DETAILED DESCRIPTION OF THE INVENTION

The invention encompasses a process for making a compound of Formula Ia or Ib

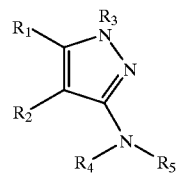

Ia

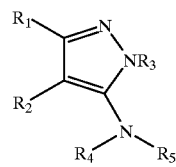

Ib wherein:

$R_1$ is selected from the group consisting, of hydrogen, alkyl, O-alkyl, O-cycloalkyl, cycloalkyl, cycloalkenyl, and a 5 or 6 membered heterocycle substituted with one or more substituents selected from the group consisting of $C_{1-3}$ alkyl, halo, OH, O-alkyl, cyano, $CF_3$, $OCF_3$ and substituted phenyl wherein the substituents are selected from the group consisting of hydrogen, halo, alkoxy, alkylthio, cyano, $CF_3$, $OCF_3$, alkyl, $SO_2CH_3$, $SO_2NH_2$, $SO_2NHCOalkyl$, $SO_2NHCOalkyl$, alkenyl, and alkynyl;

$R_2$ is selected from the group consisting of pyridyl, pyrimidyl, triazinyl, hydrogen, halo, alkyl, and mono- or di-substituted 6-membered heterocycle wherein the substituent is selected from the group consisting of hydrogen, halo, O-alkyl, S-alkyl, cyano, $CF_3$, $OCF_3$, alkyl, alkylamino, dialkylamino, and mono or di-substituted phenyl optionally substituted from the group selected from hydrogen, halo, alkoxy, alkylthio, cyano, $CF_3$, $OCF_3$, alkyl, alkylamino, and dialkylamino;

$R_3$ is selected from the group selected from hydrogen, alkyl, and phenyl, wherein all but hydrogen may optionally be substituted by one or more of the group consisting of $SO_2CH_3$, halo, alkyl, O-alkyl, S-alkyl cyano, $CF_3$, $OCF_3$, and $SO_2NH_2$;

$R_4$ is selected from the group consisting of alkyl, phenyl, cycloalkyl and heterocyclyl optionally substituted by one or more of the group consisting of OH, $NH_2$, SH, O-alkyl, $NHR_7$, $N(R_7)_2$, alkoxycarbonyl, acyl and halo;

$R_5$ is selected from the group consisting of alkyl, phenyl, cycloalkyl and heterocyclyl optionally substituted by one or more of the group consisting of OH, $NH_2$, SH, S-alkyl, O-alkyl, $NHR_7$, $N(R_7)_2$, $CO_2H$, halo, alkoxycarbonyl, acyl, heterocyclyl, cycloalkyl, heterocycloalky, and heterocyclyl;

$R_4$ and $R_5$ taken together may form a ring selected from the group consisting of morpholine, aziridine, thiomorpholine, piperidine, piperazine, and N'-piperazine; $R_7$ is selected from the group consisting of alkyl and cycloalkyl; comprising:

reacting an organometallic reagent it of the formula $R_2CH_2M$ wherein M is selected from the group consisting of Li, Na, K, and Mg, with an activated form of a carboxylic acid to produce a ketone of Formula Ic;

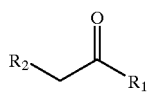

Ic treating the ketone of Formula Ic with a mixture of carbon disulfide and dihalomethane such as dibromomethane or iodochloromethane in the presence of a base and a solvent to produce the dithietane derivative of Formula Id;

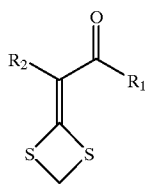

Id reacting the dithietane derivative of Formula Id with an amine of formula $R_4$—NH—$R_5$ to produce the thioamide of Formula Ie, If, or Ig;

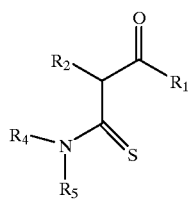

Ie

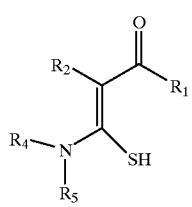

If

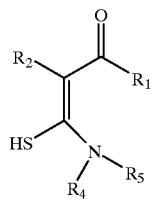

Ig condensing the thioamide of Formula Ie, If or Ig with hydrazine or substituted hydrazine.

In another embodiment of the invention is the process of making compounds of Formula IIa or IIb

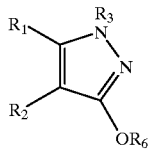

IIa

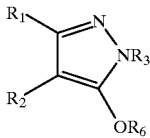

IIb wherein:

$R_1$ is selected from the group consisting of hydrogen, alkyl, O-alkyl, O-cycloalkyl, cycloalkyl, cycloalkenyl, and 5 or 6 membered heterocycle substituted with one or more substituents selected from the group consisting of $C_{1-3}$ alkyl, halo, OH, O-alkyl, cyano, $CF_3$, $OCF_3$, and substituted phenyl wherein the substituents are selected from one or more of the group consisting of hydrogen, halo, alkoxy, alkylthio, cyano, $CF_3$, $OCF_3$, alkyl, $SO_2CH_3$, $SO_2NH$, $SO_2NHCOalkyl$, $SO_2NHCOalkyl$, alkenyl, and alkynyl;

$R_2$ is selected from the group consisting of pyridyl, pyrimidyl, triazinyl, hydrogen, halo, alkyl, and mono- or di-substituted 6-membered heterocycle wherein the substituent is selected from the group consisting of hydrogen, halo, O-alkyl, S-alkyl, cyano, $CF_3$, $OCF_3$, alkyl, alkylamino, dialkylamino, and mono or di-substituted phenyl optionally substituted from the group selected from hydrogen, halo, alkoxy, alkylthio, cyano, $CF_3$, $OCF_3$, alkyl, alkylamino and dialkylamino;

$R_3$ is selected from the group selected from hydrogen, alkyl, and phenyl wherein all but hydrogen may be substituted by one or more of the group consisting of $SO_2CH_3$, halo, alkyl, O-alkyl, S-alkyl, cyano, $CF_3$, $OCF_3$, and $SO_2NH_2$;

$R_6$ is selected from the group consisting of hydrogen, alkyl, phenyl, cycloalkyl and heterocyclyl which may be optionally substituted by one or more of the group consisting of phenyl, substituted phenyl, alkoxycarbonyl, acyl, halo, OH, $NH_2$, $NHR_3$, $N(R_3)_2$, and cyano, cycloalkyl, heterocycloalkyl, and 3–7 membered heterocycle ring;

comprising:
reacting an organometallic reagent of the formula $R_2CH_2M$ wherein M is selected from the group consisting of Li, Na, K, and Mg, with an activated form of a carboxylic acid to produce a ketone of Formula IIc;

IIc treating the ketone of Formula IIc with a mixture of carbon disulfide and dihalo methane such as dibromomethane or iodochloromethane in the presence of a base and a solvent to produce the dithietane derivative of Formula IId;

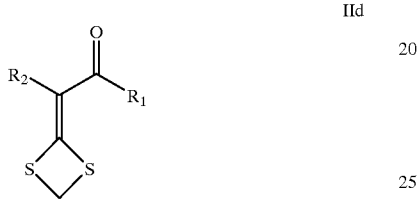

IId reacting the dithietane derivative of Formula IId with $NaOR_6$ to produce Formula IIe;

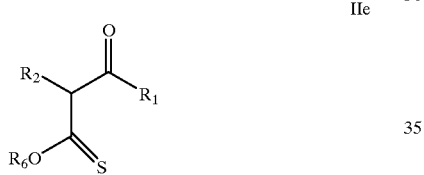

IIe condensing Formula IIe with hydrazine or substituted hydrazine.

In another embodiment of the invention is the process of making compounds of Formula IIIa or IIIb

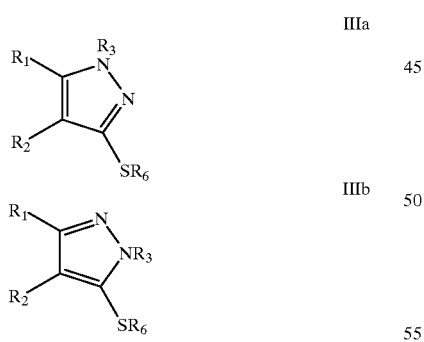

IIIa

IIIb wherein:
$R_1$ is selected from the group consisting of hydrogen, alkyl, O-alkyl, O-cycloalkyl, cycloalkyl, cycloalkenyl, and 5 or 6 membered heterocycle substituted with one or more of the substituents selected from the group consisting of alkyl, halo, OH, O-alkyl, cyano, $CF_3$, $OCF_3$, and substituted phenyl wherein the substituents are selected from the group consisting of hydrogen, halo, alkoxy, alkylthio, cyano, $CF_3$, $OCF_3$, alkyl, $SO_2CH_3$, $SO_2NH_2$, $SO_2NHCOalkyl$, $SO_2NHCOalkyl$, alkenyl, and alkynyl;

$R_2$ is selected from the group consisting of pyridyl, pyrimidyl, triazinyl, hydrogen, halo, alkyl, mono- or di-substituted 6-membered heterocycle wherein the substituent is selected from the group consisting of one or more hydrogen, halo, O-alkyl, S-alkyl, cyano, $CF_3$, $OCF_3$, alkyl, alkylamino, dialkylamino, and mono or di-substituted phenyl substituted from the group selected from hydrogen, halo, alkoxy, alkylthio, cyano, $CF_3$, $OCF_3$, alkyl, alkyl amino, and dialkylamino;

$R_3$ is selected from the group selected from hydrogen, alkyl, phenyl of which all but hydrogen may be optionally substituted by one or more of the group consisting of $SO_2CH_3$, halo, alkyl, O-alkyl, S-alkyl, cyano, $CF_3$, $OCF_3$, and $SO_2NH_2$;

$R_6$ is selected from the group consisting of hydrogen, alkyl, phenyl, cycloalkyl, and heterocyclyl which may be optionally substituted by one or more of the group consisting of phenyl, substituted phenyl, halo, alkoxycarbonyl, acyl, OH, $NH_2$, $NHR_3$, $N(R_3)_2$, and cyano, cycloalkyl, heterocycloalkyl, and 3–7 membered heterocycle ring;

comprising:
reacting an organometallic reagent of the formula $R_2CH_2M$ wherein M is selected from the group consisting of Li, Na, K, and Mg, with an activated form of a carboxylic acid to produce a ketone of Formula IIIc;

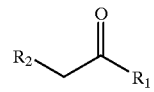

IIIc treating the ketone of Formula IIIc with a mixture of carbon disulfide and dihalomethane such as iodochloromethane or dibromomethane in the presence of a base and a solvent to produce the dithietane derivative of Formula IIId;

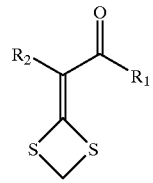

IIId reacting the dithietane derivative of Formula IIId with $R_3NHNH_2$ to produce a heterocycle of the formula IIIe or IIIf and their tautomers;

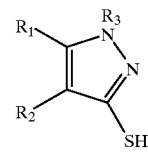

IIIe

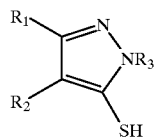

IIIf reacting the heterocycle of the formula IIIe or IIIf with an activated form of $R_6$ in the presence of a base and a solvent.

The term "alkyl", alone or in combination, means an acyclic alkyl radical containing from 1 to about 10, or from 1 to about 8 carbon atoms or 1 to about 6 carbon atoms. Said alkyl radicals may be optionally substituted. Examples of such radicals include methyl, ethyl, chloroethyl hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such radicals containing from about 2 to about 10 carbon atoms, or from about 2 to about 8 carbon atoms or 2 to about 6 carbon atoms. Said alkenyl radicals may be optionally substituted. Examples of suitable alkenyl radicals include propylenyl, 2-chloropropylenyl, buten-1-yl, isobutenyl, pentenylen-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, or about 2 to about 8 carbon atoms or 2 to about 6 carbon atoms. Said alkynyl radicals may be optionally substituted. Examples of suitable alkynyl radicals include ethynyl, propynl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "cyano" radical denote; a carbon radical having three of four covalent bonds shared by a nitrogen atom.

The term "halo" means halogens such as fluorine, chlorine, bromine or iodine atoms.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The term "heterocyclyl" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 7-membered heteromonocylic group containing 1 to 4 nitrogen atoms [e.g. pyrrolidinyl, imidazolidinyl, piperidino, piperazinyl, etc.]; saturated 3 to 7-membered heteromonocyclic group containing 1 to 2 oxygen atoms and 1 to 3 nitrogen atoms [e.g. morpholinyl, etc.]; saturated 3 to 7-membered heteromonocyclic group containing 1 to 2 sulfur atoms and 1 to 3 nitrogen atoms [e g., thiazolidinyl, etc.]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotrazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents as defined below. Heterocyclic radicals include five to ten membered fused or unfused radicals. Non-limiting examples of heterocyclic radicals include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazonyl, quinolinyl, tetraazolyl, and the like.

The term "cycloalkyl" embraces radicals having three to ten carbon atoms. Cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl-substituted alkyl radicals. Cycloalkylalkyl radicals are "lower cycloalkylalkyl" radicals having cycloalkyl radicals attached to alkyl radicals having one to six carbon atoms. Examples of such radicals include cyclohexylhexyl.

The term "cycloalkenyl" embraces radicals having three to ten carbon atoms and one or more carbon—carbon double bonds. Cycloalkenyl radicals are "lower cycloalkenyl" radicals having three to seven carbon atoms. Examples include radicals such as cyclobutenyl, cyclopentenyl, cyclohexenyl and cycloheptenyl.

The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. Halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals. The term "halocycloalkoxy" also embraces cycloalkoxy radicals having one or more halo radicals attached to the cycloalkoxy radical, that is, to form monohalocycloalkoxy, dihalocycloalkoxy, and polycycloalkoxy radicals.

The term "alkylthio" embraces radicals containing a linear or branched alkyl radical, of one to ten carbon atoms, attached to a divalent sulfur atom. Alkylthio radicals are "lower alkylthio" radicals having one to six carbon atoms. An example of "lower alkylthio" is methylthio (CH$_3$—S—). The term "alkylsulfinyl" embraces radicals containing a linear or branched alkyl radical, of one to ten carbon atoms, attached to a divalent —S(═O)— atom.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. Alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "substituted phenyl" embraces a phenyl moiety substituted at one or more carbons with one or more suitable substituent. Said substituents include alkyl, alkenyl, alkynyl, O-alkyl, S-alkyl, O-alkenyl, S-alkenyl, halo, cyano, CF$_3$, OCF$_3$, SO$_2$NH$_2$, SO$_2$CH$_3$, OH, NH$_2$, N, S, O, and the like.

Reaction Scheme 1

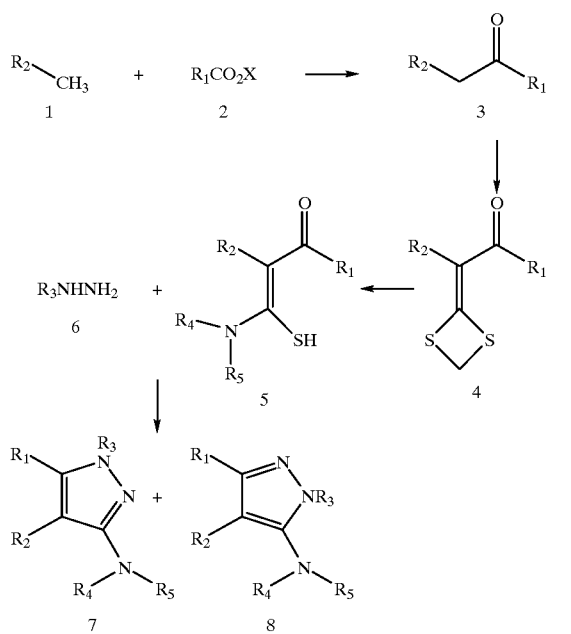

Scheme 1 shows a process for synthesis of selected 5-amino-pyrazoles. Treatment of 1 with a base such as sodium bis(trimethylsilyl)amide generates the corresponding organometallic. This organometallic reagent is then treated with an ester 2 in a suitable solvent such as tetrahydrofuran to afford the desired ketone 3. Treatment of ketone 3 with a mixture of carbon disulfide, dihalomethane, and a base such as potassium carbonate in a suitable solvent such as acetone provides the key dithietane compound 4. The dithietane compound 4 may then be reacted with an appropriate amine with or without heating in an acceptable solvent such as toluene or acetonitrile to make the thioamide compound 5. Thioamide compound 5 is treated with a mono-substituted hydrazine (6) or hydrazine (6, R═H) in an appropriate solvent such as tetrahydrofuran or an alcohol with or without heating to produce pyrazoles 7 and 8. In the case of hydrazine (6, R═H) the pyrazoles (7 and 8, R$_3$═H) thus produced are tautomers.

Reaction Scheme 2

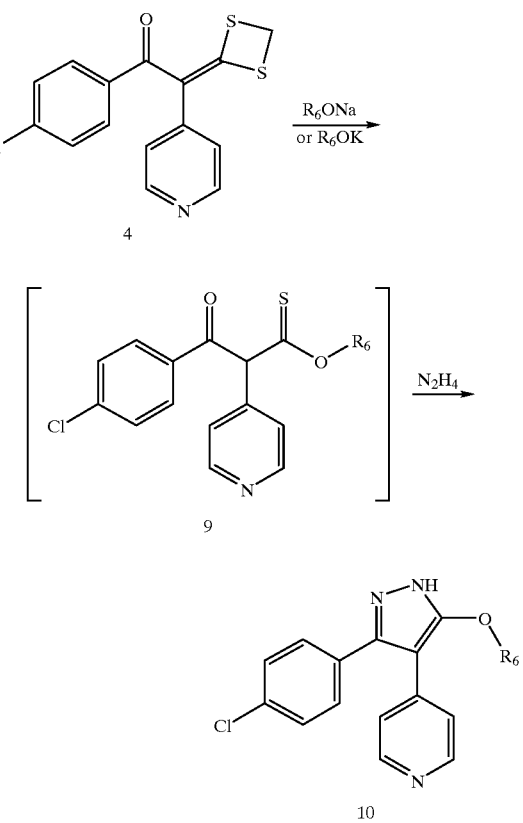

The dithietane 4 is added to a solution of a sodium or potassium alkoxide in THF. The alkoxide may be generated by treating an alcohol, in THF, with a suitable base, such as sodium hydride, NaHMDS, or KHMDS. The reaction mixture is allowed to stir from 4 to 72 hours at room temperature. The resulting thionoester 9 is allowed to react with hydrazine, or its hydrate, in ethanol, methanol, or THF at room temperature for 2–18 hours to generate the pyrazole products 10.

Reaction Scheme 3

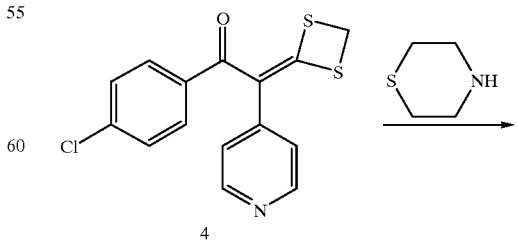

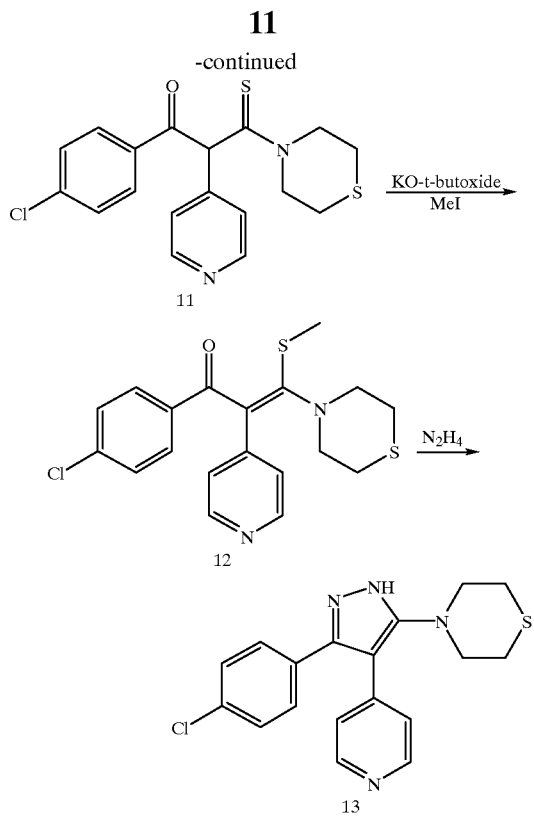

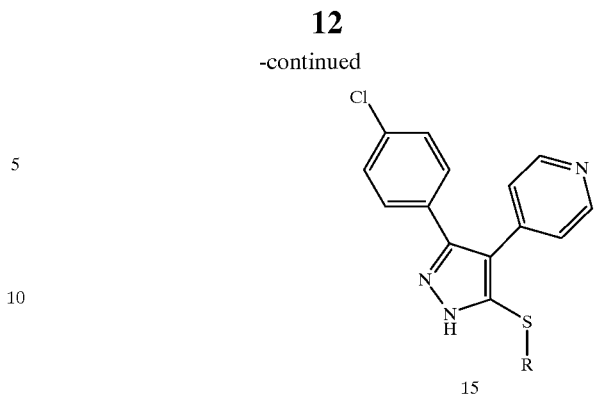

To the dithietane 4 in toluene is added at amine, such as thiomorpholine and heated from 80–110° C. The resulting thioamide 11 may be isolated or used directly in the next reaction step. To the thioamide in THF is added a suitable base, such as potassium t-butoxide and the resulting thiol anion alkylated with iodomethane. The resulting intermediate 12 can be cyclized with hydrazine, in a solvent, such as THF or ethanol, to generate the pyrazole 13.

Reaction Scheme 4

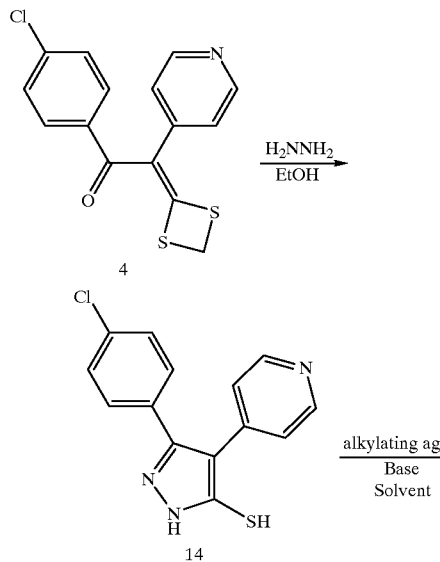

The dithietane 4 in a suitable solvent, such as THF or ethanol, is allowed to react with hydrazine, or its hydrate, at room temperature up to the reflux temperature of the solvent to generate the thiopyrazole 14. The thiol group may be alkylated with a variety of alkylating agents, such as alkyl halides or Michael acceptors, including; methyl chloroacetate, ethyl acrylate, and benzyl bromide, in the presence of a suitable base such as potassium carbonate, sodium ethoxide or triethylamine in a solvent such as DMF or ethanol to generate the desired pyrazoles 15.

Reaction Scheme 5

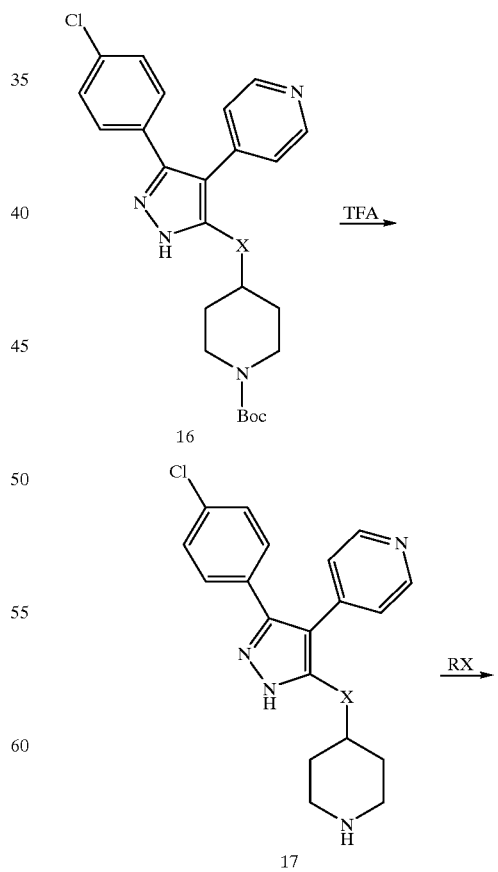

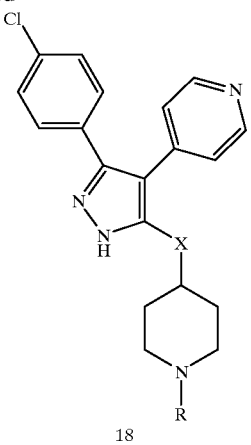

Pyrazoles, such as 16, containing acid labile amine protecting groups may be treated with a suitable acid catalyst, such as TFA in dichloromethane or HCl in ethanol or dioxane. The resulting amine 17 can then be acylated or alkylated in a straightforward fashion using a suitable base, such as potassium carbonate or triethylamine, with a reagent, such as for example; acetyl chloride or methyl iodide. In addition, N-methylation can be performed directly, using formaldehyde and formic acid in ethanol/water at reflux to give the desired pyrazoles 18.

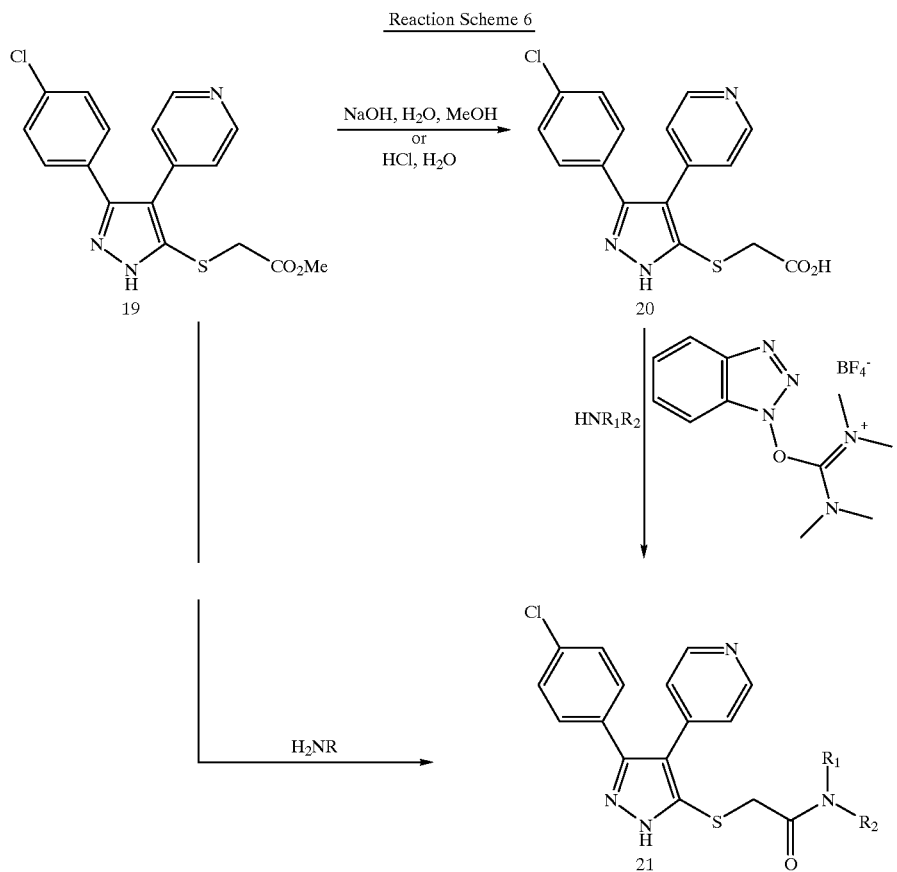

Reaction Scheme 6

Pyrazoles containing base labile esters, such as 19, may be treated with a suitable base, such as, NaOH to generate the free acid 20. The resulting acid can then aminated in a straightforward fashion using a suitable coupling reagent, such as EDC or TBTU, with or without catalysts, such as HOBt or N-hydroxysuccinimide, and an appropriate amine. In addition, amidation can be performed directly, by treating the methyl ester with an appropriate amine, for example N-methylpiperazine, in a suitable solvent such as DMF or methanol, at a temperature from room temperature up to reflux to generate the desired pyrazoles 21.

The following examples are provided to illustrate the present invention and are not intended to limit the scope thereof. Those skilled in the art will readily understand that known variations of the conditions and processes of the following preparative procedures can be used to prepare these compounds.

Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated.

The starting materials which are required for the above processes herein described are known in the literature or can be made by known methods from known starting materials.

EXAMPLE 1

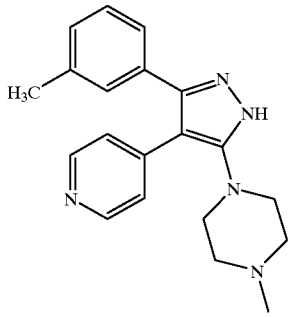

1-[5-(3-Tolyl)-4-(4-pyridinyl)-1H-pyrazol-3-yl-4-methylpiperazine

Step 1. Preparation of 1-tolyl-2-(4-pyridyl)ethanone

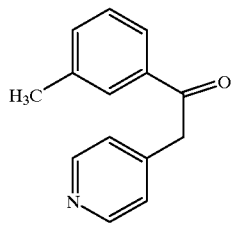

Methyl 3-methylbenzoate (6.0 g, 40 mmol), tetrahydrofuran (50 mL), and 4-picoline (4.1 g, 44 mmol) were stirred at −78° C. under an atmosphere of nitrogen. Sodium bis(trimethylsilyl)amide 1.0 M in THF (88 mL, 88 mmol) was added dropwise. The mixture was allowed to warm to room temperature and stir for 16 h when it was poured into saturated aqueos sodium bicarbonate solution. The mixture was then extracted with ethyl acetate (3×50 mL). The combined organics were washed with brine (2×50 mL), dried over magnesium sulfate, and concentrated. The product was recrystallized from ethyl acetate/hexane to yield a light yellow solid (5.7 g, 67%): mp 118.0–119.0° C. $^1$H NMR (acetone-$d_6$/300 MHz) 8.50 (m, 2H), 7.90 (m, 2H), 7.44 (m, 2H), 7.29 (m, 2H), 4.45 (s, 2H), 2.41 (s, 3H). ESHRMS m/z 212.1067 (M+H, $C_{14}H_{13}NO$ requires 212.1075).

Anal. Calc'd for $C_{14}H_{13}NO$: C, 79.59; H, 6.20; N, 6.63. Found: C, 79.54; H, 6.30; N, 6.56.

Step 2. Preparation of 1-(3-tolyl)-2-(1,3-dithietan-2-ylidene)-2-(4-pyridyl)ethanone

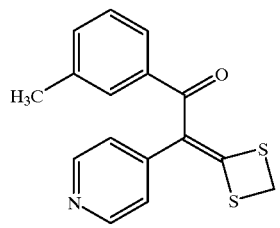

1-Tolyl-2-(4-pyridyl)ethanone (4.22 g, 20 mmol), acetone (100 mL), potassium carbonate (8.3 g, 60 mmol), carbon disulfide 4.56 g, 60 mmol), and dibromomethane (10.43 g, 60 mmol) were stirred at room temperature for 16 h. Water (100 mL) was added and the mixture was extracted with ethyl acetate (3×50 mL). The combined organic extracts were washed with brine (2×50 mL), dried over magnesium sulfate and concentrated. This crude material was purified by either flash column chromatography eluting with ethyl acetate:hexane or crystallization from ethyl acetate/hexane to yield a yellow solid (4.8 g, 80%): mp 178.6–179.2° C. $^1$H NMR (acetone-$d_6$/300) MHz) 8.47 (m, 2H), 7.08 (m, 6H), 4.37 (s, 2H), 2.21 (s, 3H). ESHRMS m/z 300.0521 (M+H, $C_{16}H_{14}NOS_2$ requires 300.0517).

Anal. Calc'd for $C_{16}H_{13}NOS_2$: C, 64.18; H, 4.38; N, 4.68. Found: C, 64.08; H, 4.25; N, 4.62.

Step 3. Preparation of 1-[3-(3-tolyl)-3-oxo-2-(4-pyridyl)-1-thiopropyl]-4-methylpiperazine

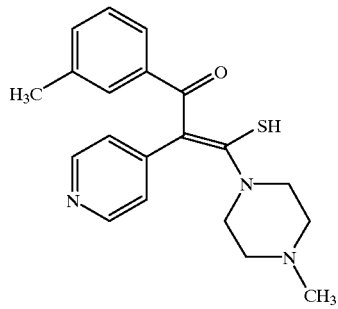

1-(3-tolyl)-2-(1,3-dithietan-2-ylidene)-2-(4-pyridyl) ethanone (3.0 g, 10 mmol), N-methylpiperazine (5.0 g, 50 mmol), and toluene (50 mL) were heated to reflux using a Dean-Stark apparatus for 1 to 3 h. The reaction was allowed to cool to room temperature and was concentrated to dryness under high vacuum. This thick, oily material was crystallized from ethyl acetate/hexane (2.9 g, 82%): mp 124.8–125.8° C. $^1$H NMR (acetone-$d_{6/300}$ MHz) 8.57 (m, 2H), 7.75 (m, 2H), 7.54 (m, 2H), 7.37 (m, 2H) 6.54 (s, 1H), 4.27 (m, 2H), 4.19 (m, 1H), 3.83 (m, 1H), 2.47–2.28 (m, 6H), 2.22 (s, 3H), 2.17 (m, 1H). ESHRMS m/z 354.1669 (M+H, $C_{20}H_{24}N_3OS$ requires 354.1640).

Anal. Calc'd for $C_{20}H_{23}N_3OS$: C, 67.96; H, 6.56; N, 11.89. Found: C, 67.79; H, 6.66; N, 11.88.

Step 4. Preparation of 1-[5-(3-tolyl)-4-(4-pyridinyl)-1H-pyrazol-3-yl-4-methylpiperazine

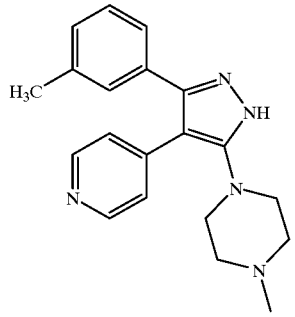

1-[3-(3-tolyl)-3-oxo-2-(4-pyridyl)-1-thiopropyl]-4-methylpiperazine (1.06 g, 3 mmol), tetrahydrofuran (50 mL), and hydrazine (15 mL, 15 mmol, 1.0 M in THF were stirred at room temperature for 16 h. A white solid was collected by filtration. Purification when necessary was by trituration or recrystallization (0.98 g, 97%): mp 261.9–262.0° C. $^1$H NMR (DMSO $d_6$/300 MHz) 12.6 (brs, 1H), 8.42 (m, 2H). 7.2 (m, 4H), 7.12 (s, 1H), 7.0 (m, 1H), 2.86 (m, 4H), 2.34 (m, 4H) 2.25 (s, 3H), 2.16 (s, 3H). ESHRMS m/z 334.2049 (M+H, $C_{20}H_{24}N_5$ requires 334.2032).

Anal. Calc'd for $C_{20}H_{23}N_5$: C, 72.04; H, 6.95; N, 21.00. Found: C, 71.83; H, 7.06; N, 20.83.

EXAMPLE 2

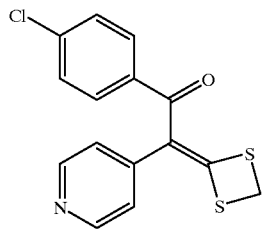

Step 1. 1-(4-chlorophenyl)-2-(4-pyridyl)ethanone was prepared according to the procedure used in example 1, step 1, Yield: 74%, yellow solid, mp 95.5–97.3° C. $^1$H-NMR (DMSO-$d_6$/300 MHz) 8.57 (br d, 2H), 7.92 (d, 2H), 7.46 (d, 2H), 7.20 (d, 2H), 4.28 (s, 2H). ESHRMS m/z 232 (M+H).

Step 2. To a solution of 1-(4-chlorophenyl)-2-(4-pyridyl) ethanone (70.0 g, 0.3 mol), dibromomethane (200 mL) and carbon disulfide (25.9 g, 0.34 mol) in acetone (800 mL) was added potassium carbonate (83.0 g, 0.6 mol). The reaction mixture was stirred at room temperature for 24 h. An additional two equivalents of potassium carbonate and one equivalent of carbon disulfide was added and the stirring was continued for another 24 h. Solvent was removed and the residue was partitioned between dichloromethane and water. The organic layer was washed with brine, dried over magnesium sulfate and filtered. The filtrate was concentrated and the crude product was stirred with 1 L of a mixture of ethyl acetate and ether (1:9) to give 78.4 g, 82% of pure product as a yellow solid, mp 185.3–185.4° C. $^1$H NMR (acetone-$d_{6/300}$ MHz) 8.49 (m, 2H), 7.31 (m, 4H), 7.09 (m, 2H), 4.39 (s, 2H). ESHRMS m/z 319.9981 (M+H, $C_{15}H_{11}ClNOS_2$ requires 319.9971).

Anal. Calc'd for $C_{15}H_{10}ClNOS_2$: C, 56.33; H, 3.15; N, 4.38. Found: C, 56.47; H, 3.13; N, 4.44.

EXAMPLE 3

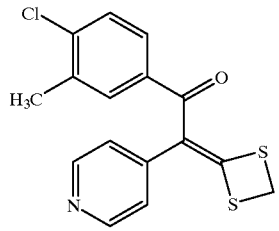

Prepared by the method described in Example 1, steps 1 and 2. mp 164.0–165.0° C. $^1$H NMR (acetone-$d_6$/300 MHz) 8.49 (m, 2H), 7.25 (m, 2H), 7.0 (m, 3H), 4.38 (s, 2H), 2.24 (s, 3H). ESHRMS m/z 334.0130 (M+H, $C_{16}H_{12}ClNOS_2$ requires 334.0127).

Anal. Calc'd for $C_{16}H_{12}ClNOS_2$: C, 57.56; H, 3.62; N, 4.20. Found: C, 57.68; H, 3.67; N, 4.17.

EXAMPLE 4

Prepared by the method described in Example 1, steps 1 and 2. mp 126.5–126.6° C. $^1$H NMR (acetone-$d_6$/300 MHz) 8.40 (m, 2H), 7.17 (m, 2H), 7.0 (m, 4H), 4.39 (s, 2H), 2.85 (s, 3H). ESHRMS m/z 300.0483 (M+H, $C_{16}H_{14}NOS_2$ requires 300.0517).

Anal. Calc'd for $C_{16}H_{13}NOS_2$: C, 64.18; H, 4.38; N, 4.68. Found: C, 64.05; H, 4.27; N, 4.59.

EXAMPLE 5

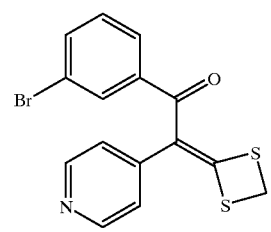

Prepared by the method described in Example 1, steps 1 and 2. mp 159.6–159.7° C. $^1$H NMR (acetone-$d_6$/300 MHz) 8.52 (m, 2H), 7.6 (m, 1H), 7.50 (s, 1H), 7.21 (m, 2H), 7.13 (m, 2H), 4.40 (s, 2H). ESHRMS m/z 363.9503 (M+H, $C_{15}H_{11}BrNOS_2$ requires 363.9465).

Anal. Calc'd for $C_{15}H_{10}BrNOS_2$: C, 49.46; H, 2.77; N, 3.84. Found: C, 49.51; H, 2.68; N, 3.74.

EXAMPLE 6

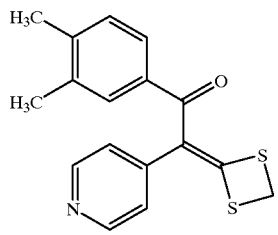

Prepared by the method described in Example 1, steps 1 and 2. mp 198.8–198.9° C. $^1$H NMR (acetone-$d_6$/300 MHz) 8.45 (m, 2H), 7.05 (m, 3H), 6.95 (m, 1H), 6.82 (m, 1H), 4.29 (s, 2H), 2.14 (s, 3H), 2.08 (s, 3H). ESHRMS m/z 314.0691 (M+H, $C_{17}H_{16}NOS_2$ requires 314.0673).

EXAMPLE 7

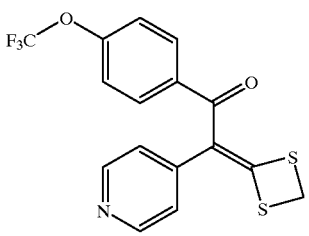

Prepared by the method described in Example 1, steps 1 and 2. mp 182.6–183.0° C. $^1$H NMR (acetone-$d_6$/300 MHz) 8.50 (m, 2H), 7.42 (d, 2H, J=8.5 Hz), 7.23 (d, 2H, J=8.5 Hz), 7.10 (m, 2H), 4.40 (s, 2H). ESHRMS m/z 370.0173 (M+H, $C_{16}H_{11}F_3NO_2S_2$ requires 370.0183).

EXAMPLE 8

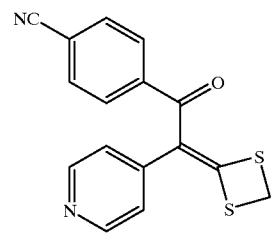

Prepared by the method described in Example 1, steps 1 and 2. mp 193.3–193.4° C. $^1$H NMR (acetone-$d_{6/300}$ MHz) 8.49 (m, 2H), 7.69 (d, 2H, J=8.2 Hz), 7.46 (d, 2H, J=8.2 Hz), 7.01 (m, 2H), 4.43 (s, 2H). ESHRMS m/z 311.0327 (M+H, $C_{16}H_{11}N_2OS_2$ requires 311.0313).

EXAMPLE 9

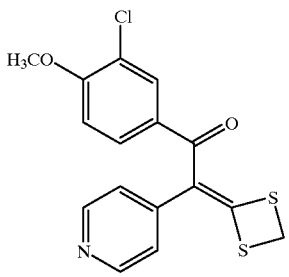

Prepared by the method described in Example 1, steps 1 and 2. mp 191.5–192.5° C. $^1$NMR (CDCl$_3$/300 MHz) 8.55 (dd, 2H, J=4.6, 1.6 Hz), 7.4 (m, 1H), 7.09–7.03 (m, 3H), 6.67 (d, 1H, J=8.7 Hz), 4.17 (s, 2H), 3.86 (s, 3H). ESHRMS m/z 350.0090 (M+H, $C_{16}H_{13}ClNO_2S_2$ requires 350.0076).

Anal. Calc'd. for $C_{16}H_{12}ClNO_2S_2$: C, 54.93; H, 3.60; N, 4.00; Cl, 10.13; S, 18.33. Found: C, 54.74; H, 3.60; N, 3.89; Cl, 10.45; S, 18.32.

EXAMPLE 10

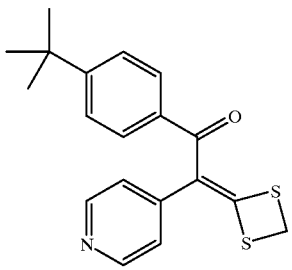

Prepared by the method described in Example 1, steps 1 and 2. mp 172.1–173.1° C. $^1$H NMR (CDCl$_3$/300 MHz) 8.51 (dd, 2H, J=4.4, 1.6 Hz), 7.23–7.21 (m, 4H), 7.04 (dd, 2H, J=4.6, 1.6 Hz), 4.17 (s, 2H), 1.25 (s, 9H). ESHRMS m/z 342.1004 (M+H, $C_{19}H_{20}NOS_2$ requires 342.0986).

Anal. Calc'd for $C_{19}H_{19}NOS_2$: C, 66.83; H, 5.61; N, 4.10; S, 18.78. Found: C, 66.97; H, 5.89; N, 4.02; S, 18.64.

EXAMPLE 11

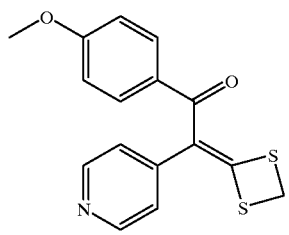

Prepared by the method described in Example 1, steps 1 and 2. mp 203.0–204.1° C. $^1$H NMR (CDCl$_3$/300 MHz) 8.52 (dd, 2H, J=4.4, 1.6 Hz), 7.29 (d, 1H, J=6.8 Hz), 7.28 (d, 1H, J=7.0 Hz), 7.05 (dd, 2H, J=4.4, 1.6 Hz), 6.70 (d, 1H, J=6.8 Hz), 6.69 (d, 1H, J=6.8 Hz), 4.17 (s, 2H), 3.79 (s, 3H). ESHRMS m/z 316.0475 (M+H, $C_{16}H_{14}NO_2S_2$ requires 316.0466.)

Anal. Calc'd. for $C_{16}H_{13}NO_2S_2$: C, 60.93; H, 4.15; N, 4.44; S, 20.33. Found: C, 60.46; H, 4.17; N, 4.37; S, 19.84.

EXAMPLE 12

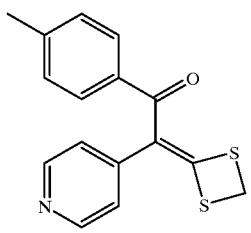

Prepared by the method described in Example 1, steps 1 and 2. mp 209.1–215.1° C. $^1$H NMR (CDCl$_3$/300 MHz) 8.50 (dd, 2H, J=4.4, 1.6 Hz), 7.20 (d, 2H, J=8.0 Hz), 7.03–6.99 (m, 4H), 4.18 (s, 2H), 2.30 (s, 3H). ESHRMS m/z 300.0517 (M+H, C$_{16}$H$_{14}$NOS$_2$ requires 300.0517).

Anal. Calc'd. for C$_{16}$H$_{13}$NOS$_2$: C64.18; H, 4.38; N, 4.69; S, 21.42. Found: C, 64.02; H, 4.62; N, 4.54; S, 21.24.

EXAMPLE 13

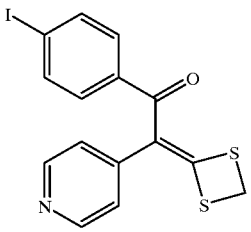

Prepared by the method described in Example 1, steps 1 and 2. mp 257.6–257.7° C. $^1$H NMR (CDCl$_3$/300 MHz) 8.51 (dd, 2H, J=4.4, 1.6 Hz), 7.57 (d, 2H, J=8.5 Hz), 7.27–6.99 (m, 4H), 4.18 (s, 2H). ESHRMS m/z 411.9348 (M+H, C$_{15}$H$_{11}$NIOS$_2$ requires 411.9327).

Anal. Calc'd. for C$_{15}$H$_{10}$NIOS$_2$: C, 43.81; H, 2.45; N, 3.41. Found: C, 43.71; H, 2.27; N, 3.41.

EXAMPLE 14

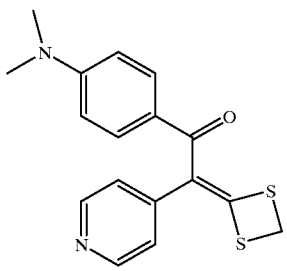

Prepared by the method described in Example 1, steps 1 and 2. mp 197.3–202.2° C. $^1$H NMR (CDCl$_3$/300 MHz) 8.53(dd, 2H, J=4.4, 1.6 Hz), 7.26 (d, 2H, J=9.3 Hz), 7.09 (dd, 2H, J=4.4, 1.6 Hz), 6.43 (d, 2H, J=9.3 Hz), 4.14 (s, 2H), 2.97 (s, 6H). ESHRMS m/z 329.0789 (M+H, C$_{17}$H$_{17}$N$_2$OS$_2$ requires 329.0782).

Anal. Calc'd. for C$_{17}$H$_{16}$N$_2$OS$_2$: C, 62.17; H, 4.91; N, 8.53; S, 19.53. Found: C, 61.93; H, 5.12; N, 8.46; S, 19.26.

EXAMPLE 15

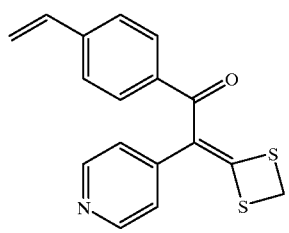

Prepared by the method described in Example 1, steps 1 and 2. mp 176.6–176.7° C. $^1$H NMR (CDCl$_3$/300 MHz) 8.51 (dd, 2H, J=4.4, 1.6 Hz), 7.29–7.22 (m, 4H), 7.03 (dd, 2H, J=4.4, 1.6 Hz), 6.64 (dd, 1H, J=17.5, 10.9 Hz), 5.76 (d, 1H, J=17.7 Hz), 5.31 (d, 1H, J=10.9 Hz), 4.19 (s, 2H). ESHRMS 312.0513 (M+H, C$_{17}$H$_{14}$NOS$_2$ requires 312.0517).

Anal. Calc'd. for C$_{17}$H$_{13}$NOS$_2$: C, 65.56; H, 4.21; N, 4.50. Found: C, 65.75; H, 4.11; N, 4.46.

EXAMPLE 16

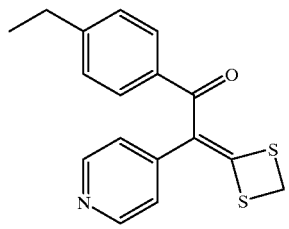

Prepared by the method described in Example 1, steps 1 and 2. mp 174.8–175.0° C. $^1$H NMR (CDCl$_3$/300 MHz) 8.50 (dd, 2H, J=4.4, 1.6 Hz), 7.23–7.20 (m, 4H), 7.03 (dd, 2H, J=4.6, 1.6 Hz), 4.17 (s, 2H), 2.59 (q, 2H, J=7.6 Hz), 1.17 (t, 3H, J=7.7 Hz). ESHRMS m/z 314.0677 (M+H, C$_{17}$H$_{16}$NOS$_2$ requires 314.0673).

Anal. Calc'd. for C$_{17}$H$_{15}$NOS$_2$: C, 65.14; H, 4.82; N, 4.47. Found: C, 64.90; H, 4.62; N, 4.45.

EXAMPLE 17

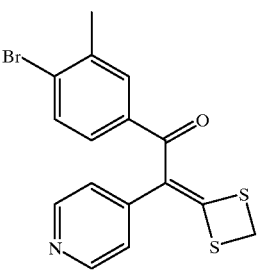

Prepared by the method described in Example 1, steps 1 and 2. mp 167.1–167.5° C. $^1$H NMR (CDCl$_3$/300 MHz) 8.52 (dd, 1H, J=4.4, 1.6 Hz), 7.33 (d, 1H, J=8.3 Hz), 7.02–7.00 (m, 3H), 6.87–6.83 (m, 1H), 4.19 (s, 2H), 2.28 (s, 3H). ESHRMS m/z 379.9577 (M+H, C$_{16}$H$_{13}$BrNOS$_2$ requires 379.9622).

Anal. Calc'd. for C$_{16}$H$_{12}$BrNOS$_2$: C, 50.80; H, 3.20; N, 3.70. Found: C, 50.69; H, 3.19; N, 3.71.

EXAMPLE 18

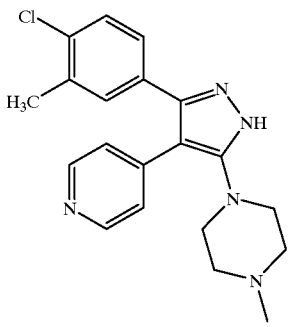

Prepared from Example 3 by the method described in Example 1, steps 3 and 4. mp 236.7–239.3° C. $^1$H NMR (DMSO-$d_6$/300 MHz) 12.6 (brs, 1H), 8.45 (m, 2H), 7.41 (m, 1H), 7.26 (m, 3H), 7.0 (m, 1H), 2.86 (m, 4H), 2.35 (m, 4H), 2.27 (s, 3H), 2.16 (s, 3H). ESHRMS m/z 368.4653 (M+H, $C_{20}H_{23}ClN_5$ requires 368.1642).

EXAMPLE 19

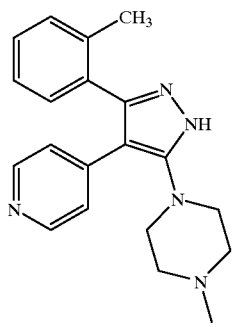

Prepared from Example 4 by the method described in Example 1, steps 3 and 4. mp 244.0–244.2° C. $^1$H NMR (acetone-$d_6$/300 MHz) 11.6 (brs, 1H), 8.35 (m, 2H), 7.35 (m, 2H), 7.25 (m, 4H), 3.05 (m, 4H), 2.47 (m, 4H), 2.25 (s, 3H), 2.00 (s, 3H). ESHRMS m/z 334.2018 (M+H, $C_{20}H_{24}N_5$ requires 334.2032).
Anal. Calc'd for $C_{20}H_{23}N_5$: C, 72.04; H, 6.95; N, 21.00. Found: C, 72.03; H, 7.00; N, 20.85.

EXAMPLE 20

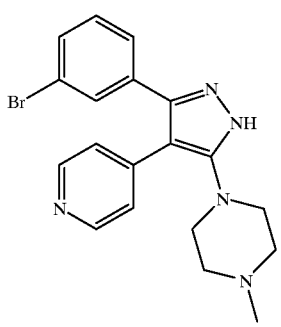

Prepared from Example 5 by the method described in Example 1, steps 3 and 4. mp 222.5–223.4° C. $^1$H NMR (acetone-$d_6$/300 MHz) 11.8 (brs, 1H), 8.51 (m, 2H), 7.55 (m, 2H), 7.34 (m, 4H), 3.0 (m, 4H), 2.41 (m, 4H), 2.22 (s, 3H). ESHRMS m/z 398.0982 (M+H, $C_{19}H_{21}BrN_5$ requires 398.0980).

EXAMPLE 21

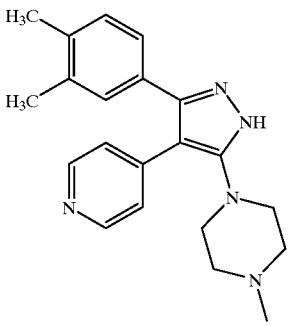

Prepared from Example 6 by the method described in Example 1, steps 3 and 4. mp 270.9–272.7° C. $^1$H NMR (DMSO-$d_6$/300 MHz) 12.5 (brs, 1H), 8.41 (m, 2H), 7.24 (m, 2H), 7.26 (m, 3H), 7.10 (m, 2H), 6.92 (m, 1H), 2.86 (m, 4H), 2.38 (m, 4H) (s, 3H), 2.19 (s, 3H), 2.16 (s, 3H). ESHRMS m/z 348.2183 (M+H, $C_{22}H_{25}N_5$ requires 348.2188).

EXAMPLE 22

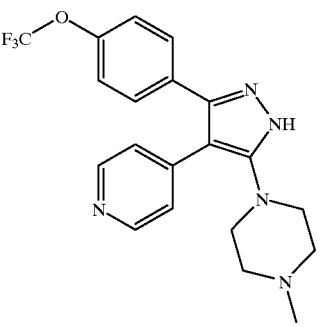

Prepared from Example 7 by the method described in Example 1, steps 3 and 4. mp 221.0–221.2° C. $^1$H NMR (DMSO-$d_6$/300 MHz) 12.7 (brs, 1H), 8.45 (m, 2H), 7.38 (s, 4H), 7.24 (m, 2H), 2.86 (m, 4H), 2.34 (m, 4H), 2.16 (s, 3H). ESHRMS m/z 404.1698 (M+H, $C_{20}H_{21}F_3N_5O$ requires 404.1698).

EXAMPLE 23

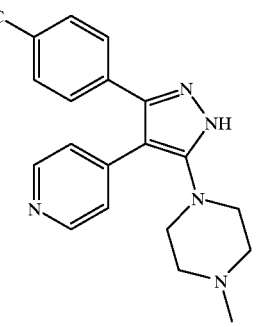

Prepared from Example 8 by the method described in Example 1, steps 3 and 4. mp >300° C. $^1$H NMR (DMSO-$d_6$/300 Mz) 12.8 (brs, 1H), 8.47 (m, 2H), 7.83 (m, 2H), 7.42 (m, 2H), 2.88 (m, 4H), 2.39 (m, 4H), 2.20 (s, 3H). ESHRMS m/z 345.1848 (M+H, $C_{20}H_{21}N_6$ requires 345.1828).

EXAMPLE 24

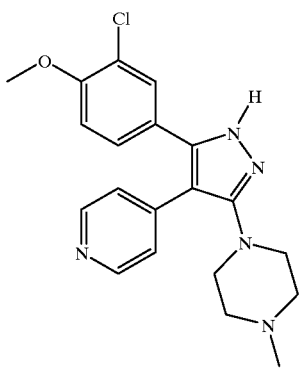

Prepared from Example 9 by the method described in Example 1, steps 3 and 4. mp 272.7–276.4° C. $^1$H NMR (DMSO-d$_6$/300 MHz) 8.44 (dd, 2H, J=4.6, 1.6 Hz), 7.32–7.13 (m, 5H), 3.84 (s, 3H), 2.90–2.85 (m, 4H), 2.38–2.35 (m, 4H), 2.16 (s, 3H). ESHRMS m/z 384.1580 (M+H C$_{20}$H$_{23}$ClN$_5$O requires 384.1591).

EXAMPLE 25

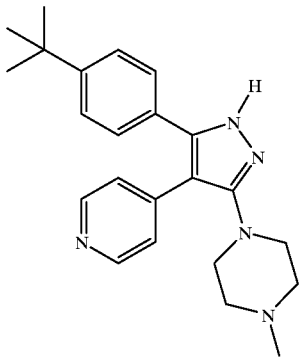

Prepared from Example 10 by the method described in Example 1, 3 and 4. mp 243.6–244.3° C. $^1$H NMR (DMSO-d$_6$/300 MHz) 8.44 (dd, 2H, J=4.6, 1.6, Hz), 7.40 (d, 2H, J=8.3 Hz), 7.28–7.18 (m, 4H), 2.90–2.85 (m, 4=H), 2.38–2.34 (m, 4H), 2.16 (s, 3H), 1.26 (s, 9H). ESHRMS m/z 376.2491 (M+H, C$_{23}$H$_{30}$N$_5$ requires 376.2501).

EXAMPLE 26

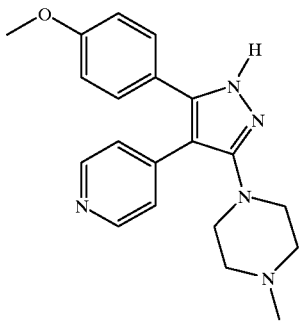

Prepared from Example 11 by the method described in Example 1, steps 3 and 4. mp 259.0–260.2° C. $^1$H NMR (DMSO-d$_6$/300 MHz) 8.53 (dd, 2H, J=4.4, 1.6 Hz), 7.24 (dd, 2H, J=4.4, 1.6 Hz), 7.18 (d, 2H, J=8.9 Hz), 6.94 (d, 2H, J=8.9 Hz), 3.75 (s, 3H), 2.90–2.85 (m, 4H), 2.39–2.35 (m, 4H), 2.16 (s, 3H). ESHRMS m/z 350.1991 (M+H, C$_{20}$H$_{24}$N$_5$O requires 350.1981).

Anal. Calc'd. for C$_{20}$H$_{23}$N$_5$O+3.93% H$_2$O: C, 66.04; H, 6.81; N, 19.25. Found: C, 66.01; H, 6.62; N, 19.32.

EXAMPLE 27

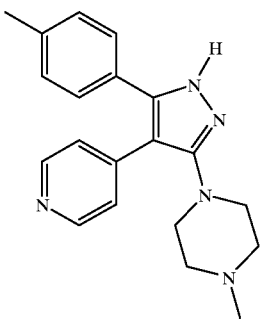

Prepared from Example 12 by the method described in Example 1, steps 3 and 4. mp 243.0–246.8° C. $^1$H NMR (DMSO d$_6$/300 MHz) 8.41 (dd, 2H, J=4.6, 1.6 Hz), 7.24 (m, 6H), 2.91–2.86 (m, 4H), 2.40–2.35 (m, 4H), 2.29 (s, 3H), 2.16 (s, 3H). ESHRMS m/z 334.2041 (M+H, C$_{20}$H$_{24}$N$_5$ requires 334.2032).

Anal. Calc'd for C$_{20}$H$_{23}$N$_5$+4.09% H$_2$O: C, 69.10; H, 7.13; N, 20.14. Found: C, 69.10; H, 7.08; N, 20.13.

EXAMPLE 28

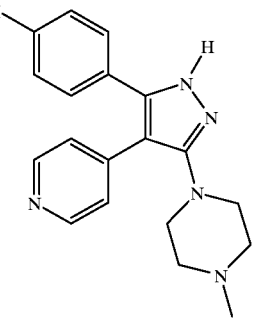

Prepared from Example 13 by the method described in Example 1, steps 3 and 4. mp 265.2–265.8° C. $^1$H NMR (CD$_3$OD/300 MHz) 8.41 (dd, 2H, J=4.6, 1.6 Hz), 7.76–7.74 (m, 2H), 7.41–7.39 (m, 2H), 7.08–7.05 (m, 2H), 3.08–3.04 (m, 4H), 2.61–2.58 (m, 4H), 2.35 (s, 3H). ESHRMS m/z 446.0847 (M+H, C$_{19}$H$_{21}$IN$_5$ requires 446.084169).

Anal. Calc'd. for C$_{19}$H$_{20}$IN$_5$+12.09% H$_2$O: C, 44.60; H, 5.39; N, 13.69. Found: C, 44.50; H, 4.56; N, 13.66.

EXAMPLE 29

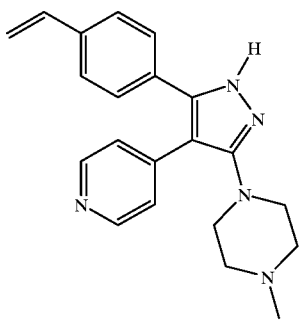

Prepared from Example 15 by the method described in Example 1, steps 3 and 4. mp>300° C. $^1$H NMR (CD$_3$OD/300 MHz) 8.49 (dd, 2H, J=4.6, 1.6 Hz), 7.47– 7.44 (m, 4H), 7.26 (d, 2H, J=8.4 Hz), 6.75 (dd, J=17.7, 11.1 Hz), 5.83 (d, 1H, J=17.5 Hz), 5.28 (d, 1H, J=11.1 Hz), 3.07–3.03 (m, 4H), 2.58–2.53(m, 4H), 2.31 (s, 3H). ESHRMS m/z 346.2034 (M+H, C$_{21}$H$_{24}$N$_5$ requires 346.2032).

Anal. Calc'd. for C$_{21}$H$_{23}$N$_5$+2.83% H$_2$O: C, 70.95; H, 6.84; N, 19.70. Found: C, 70.97; H, 6.49; N, 19.54.

EXAMPLE 30

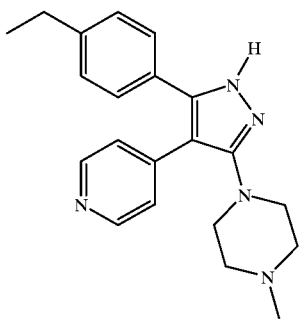

Prepared from Example 16 by the method described in Example 1, steps 3 and 4. mp 221.6–222.6° C. $^1$H NMR (CD$_3$OD/300 MHz) 8.38 (dd, 2H, J=4.6, 1.6 Hz), 7.44–7.40 (m, 2H), 7.26–7.19 (m, 4H), 3.06–3.02 (m, 4H), 2.66 (q, 2H, J=7.5 Hz), 2.59–2.54 (m, 4H), 2.32 (s, 3H), 1.23 (t, 3H, J=7.5 Hz). ESHRMS m/z 348.2188 (M+H, C$_{21}$H$_{26}$N$_5$ requires 348.2188).

Anal. Calc'd for C$_{21}$H$_{25}$N$_5$+2.5% H$_2$O: C, 70.71; H, 7.35; N, 19.63. Found: C, 70.76; H, 7.40; N, 19.46.

EXAMPLE 31

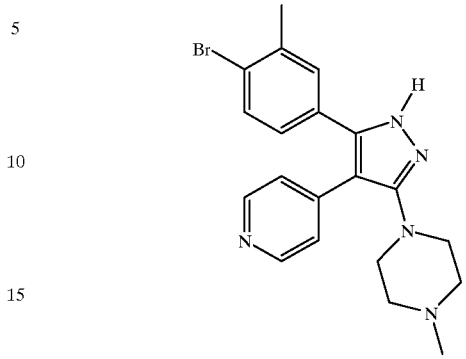

Prepared from Example 17 by the method described in Example 1, steps 3 and 4. mp 294.7° C. decomp. $^1$H NMR (CD$_3$OD/300 MHz) 8.41 (dd, 2H, J=4.6, 1.6 Hz), 7.55 (d, 1H, J=8.2 Hz), 7.45–7.42 (m, 2H), 7.27–7.25 (m, 1H), 7.00–6.97 (m 2H), 3.08–3.03 (m, 4H), 2.59–2.54 (m, 4H), 2.35 (s, 3H), 2.31 (s, 3H). ESHRMS m/z 412.1124 (M+H, C$_{20}$H$_{23}$BrN$_5$ requires 412.1137).

EXAMPLE 32

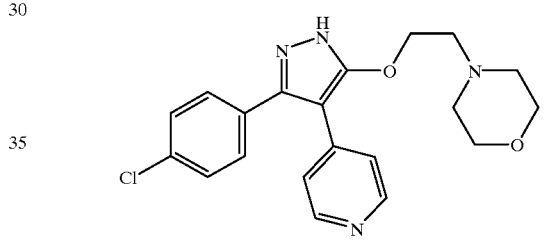

To N-(2-hydroxyethyl)morpholine (363 uL, 3 mmol) in anhydrous THF (7 mL), under nitrogen, was added 1M sodium bis(trimethylsilyl)amide (3 ml, 3 mmol) in THF at ambient temperature. The reaction mixture was stirred for 15 minutes, then the dithietane of Example 2 (636 mg, 2 mmol) was added as a solid. The reaction mixture gradually became dark orange. After about 18 hours at ambient temperature, the reaction was quenched with saturated sodium bicarbonate solution (30 mL) and extracted twice with ethyl acetate (30 mL). The organic solutions were combined and washed with saturated NaCl solution (20 mL), then dried (MgSO$_4$), filtered, and concentrated to an orange oil. The oil was taken up in MeOH (10 mL) and reconcentrated to remove any remaining ethyl acetate. The oil was then taken up in methanol (5 mL) and anhydrous hydrazine (69 uL) was added. The reaction mixture was allowed to stir at ambient temperature 18 hours, then quenched with saturated sodium bicarbonate solution (30 mL) and extracted twice with ethyl acetate (30 mL). The organic solutions were combined and washed with water (20 mL) and saturated NaCl solution (20 mL), then dried (MgSO$_4$), filtered, and concentrated to an orange semi-solid. The solid was triturated with acetonitrile (5 mL), collected by suction filtration, washed with acetonitrile and dried in-vacuo. Yield; off-white solid, 114 mg, 14.8%, mp 198.9–199.9° C. ¹H-NMR (DMSO-d₆/300 MHz) 12.61 (br s, 1H), 8.41 (d, 2H ), 7.52 (d, 2H), 7.38 (d, 2H), 7.21 (d, 2H), 4.33 (t, 2H), 3.54 (m, 4H), 2.70 (t, 2H), 2.14 (m 4H). ESHRMS m/z 385.1444 (M+H, C$_{20}$H$_{22}$ClN$_4$O$_2$ requires 385.1431).

EXAMPLE 33

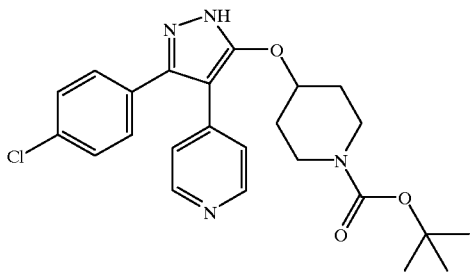

The product was prepared in an analogous manner to that of Example 32, starting with 4-hydroxy-N-t-boc piperidine. Recrystallized from acetone/methanol. Yield; white solid 263 mg, 29%, mp 230.1–231.8° C. ¹H-NMR (DMSO-d₆/ 300 MHz) 12.61 (br s, 1H), 8.42 (d, 2H), 7.52 (d, 2H), 7.38 (d, 2H), 7.20 (d, 2H), 4.88 (m, 1H), 3.52 (m, 2H), 3.30 (m, 2H), 1.93 (m, 2H), 1.65 (m, 2H), 1.39 (s, 9H).

Anal. Calc'd for C$_{24}$H$_{27}$ClN$_4$O$_3$: C, 63.36; H, 5.98; N, 12.31. Found: C, 63.34; H, 5.97; N, 12.22.

EXAMPLE 34

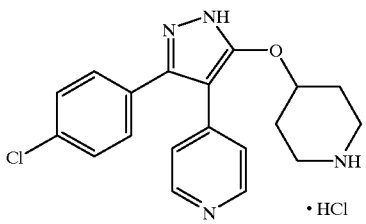

The product from Example 33 (130 mg, 0.28 mmol) was treated with conc. HCl (0.5 mL) in ethanol (5 mL) for 2 hours. The solvent was removed in-vacuo and the resulting residue dissolved in ethanol and reconcentrated twice. The resulting solid was triturated with acetonitrile to afford a white solid. Yield, 119 mg, 91%, trihydrochloride salt, mp 220.6–222.1° C. ¹H-NMR (DMSO-d₆/300 MHz) 13.25 (br s, 1H), 9.10 (br s, 2H), 8.67 (d, 2H), 7.75 (d, 2H), 7.60 (d, 2H), 7.50 (d, 2H), 5.04 (m, 1H), 3.17 (br d, 4H), 2.21 (m, 2H), 2.03 (m, 2H).

Anal. Calc'd for C$_{19}$H$_{19}$ClN$_4$O 3 HCl: C, 49.16; H, 4.78; N, 12.07. Found: C, 49.24; H, 4.72; N, 12.02.

EXAMPLE 35

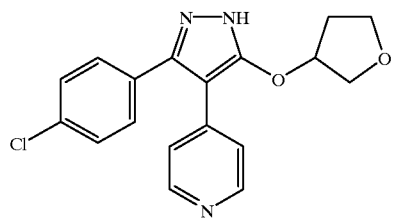

The product was prepared in a manner, analogous to Example 32 starting with (+/−)3-hydroxytetrahydrofuran. Recrystallized from ethanol. Yield; white crystalline solid, 57 mg, 8%, mp>300° C. ¹H-NMR (DMSO-d₆/300 MHz) 12.65 (br s, 1H), 8.42 (d, 2H), 7.52 (d, 2H), 7.38 (d, 2H) 7.18 (d, 2H), 5.28 (m, 1H), 3.86 (m, 2H), 3.82 (m, 1H), 3.75 (m, 1H), 2.26–2.01 (br m, 2H).

Anal. Calc'd for C$_{18}$H$_{16}$ClN$_3$O$_2$: C, 63.25; H, 4.72; N, 12.29. Found: C, 63.12; H, 4.51; N, 12.31.

EXAMPLE 36

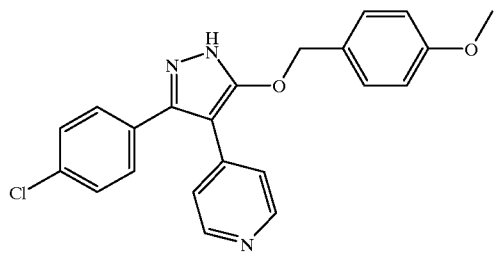

The product was prepared in a manner analogous to Example 32 starting with p-methoxybenzyl alcohol. Yield; off-white solid, 252 mg, 21%, mp=229.1–229.2° C. ¹H-NMR (acetone-d₆/300 MHz) 11.62 (br s, 1H), 8.40 (br s, 2H), 7.76 (s, 2H), 7.39 (m, 4H), 7.30 (br s, 2H), 6.87 (d, 2H), 5.21 (s, 2H), 3.77 (s, 3H).

Anal. Calc'd for C$_{22}$H$_{18}$ClN$_3$O$_2$0.25 H$_2$O: C, 66.67; H, 4.70; N, 10.60. Found: C, 66.79; H, 4.95; N, 10.54.

EXAMPLE 37

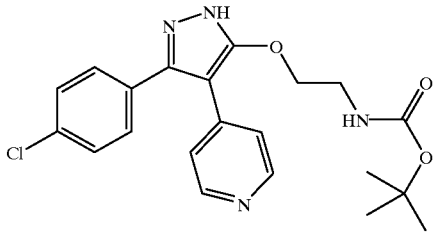

The product was prepared in a manner analogous to Example 32 starting with N-Boc-ethanolamine. Recrystallized from ethyl acetate/methanol. Yield; white solid, 75 mg, 4%, mp>300° C. ¹H-NMR (DMSO-d₆/300 MHz) 12.60 (br s, 1H), 8.38 (d, 2H), 7.53 (d, 2H), 7.38 (d, 2H), 7.22 (d, 2H), 7.02 (t, 1H), 4.20 (t, 2H), 3.34 (m, 2H), 1.36 (s, 9H). ESHRMS m/z 415.1551 (M+H, C$_{21}$H$_{24}$ClN$_4$O$_3$ requires 415.1537).

EXAMPLE 38

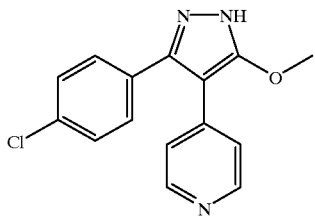

The example was prepared in a manner analogous to Example 32 starting with methanol. Yield; off-white solid, 119 mg, 14%, mp=265.3–265.3° C. $^1$H-NMR (DMSO-$d_{6/300}$ MHz) 12.61 (br s, 1H), 8.41 (d, 2H), 7.52 (d, 2H), 7.38 (d, 2H), 7.17 (d, 2H), 3.90 (s, 3H). ESHRMS m/z 286.0766 (M+H, $C_{15}H_{13}ClN_3O$ requires 286.0747).

Anal. Calc'd for $C_{15}H_{12}ClN_3O$ 0.25 $H_2O$: C, 62.08; H, 4.34; N, 14.48. Found: C, 62.24; H, 4.11; N, 14.16.

EXAMPLE 39

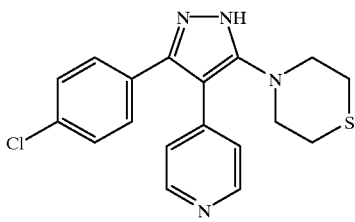

To the dithietane of Example 2 (638 mg, 2 mmol) in toluene (15 mL) was added thiomorpholine (800 uL, 8 uL). The reaction mixture was heated to reflux for 6 hours, then cooled to room temperature and diluted with toluene (20 mL). The reaction mixture was then extracted twice with water (20 mL) and brine (20 mL). The organic solution was dried (MgSO$_4$), filtered, and concentrated to an oil. Hexane was added to the residue and heated to reflux, then decanted. The oil became semi-solid. The semi-solid was dissolved in tetrahydrofuran (10 mL) and potassium t-butoxide 1M in THF (2 ml, 2 mmol) was added. This was followed by iodomethane (125 uL, 2 mmol). The reaction was stirred at room temperature for 1 hour, then quenched with water (20 ml ). The reaction mixture was extracted with ethyl acetate (2×30 mL). The organic layers were pooled, washed with brine (20 mL) and dried (MgSO$_4$). Filtration and concentration produced an oil which was chased once with toluene to remove any ethyl acetate. The residue was dissolved in ethanol (10 mL) and hydrazine hydrate (9 uL, 2 mmol) was added. The reaction mixture was stirred at room temperature fear 4 hours then partitioned between ethyl acetate and saturated sodium bicarbonate solution (30 mL each). The layers were separated and the aqueous layer extracted again with ethyl acetate (30 mL). The combined organic layers were washed with brine (20 mL) and dried (MgSO$_4$). Filtration and concentration produced an orange residue which was triturated with acetonitrile to generate a tan solid. Yield 295 mg, 43%, mp>300° C. $^1$H NMR (DMSO-$d_{6/300}$ MHz) 12.70 (br s, 1H), 8,47 (d, 2H), 7.46 (d, 2H), 7.26 (m, 4H), 3.13 (m, 4H), 2.62 (m, 4H). ESHRMS m/z 357.0942 (M+H, $C_{18}H_{18}ClN_4S$ requires 357.0941).

Anal. Calc'd for $C_{18}H_{17}ClN_4S$: C, 60.58; H, 4.80; N, 15.70. Found: C, 60.32; H, 4.96; N, 15.60.

EXAMPLE 40

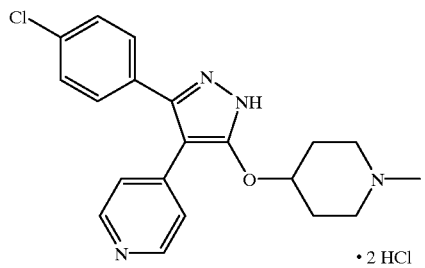

The product of Example 33 (455 mg, 1.5 mmol) was combined with 98% formic acid (6 mL) and heated to 100 C. After 3 hours, 37% formaldehyde (1.22 mL, 15 mmol) was added and the reaction was seated for an additional 5 hours at 100 C. The reaction mixture was allowed to cool to room temperature and filtered. The solution was diluted with water (15 mL) and extracted once with ethyl acetate (30 mL). The aqueous solution was then basified with 2.5 N NaOH to pH 8. The cloudy mixture was then extracted twice with 1:1 THF:EtOAc (30 mL). The organic layers were pooled and washed once with brine (25 mL), dried (MgSO$_4$), filtered and concentrated to an oil which solidified on standing. The solid was triturated with acetonitrile and collected by suction filtration. The solid was suspended in ethanol:water 2:1 (15 mL) and 1 mL of conc. HCl was added. The solution was allowed to stir at room temperature for 1 hour, then filtered and concentrated. The residue was combined with ethanol (10 mL) and reconcentrated twice. The resulting solid was triturated with acetonitrile (10 mL) containing a small amount of ethanol (0.5 mL) to remove some colored impurities. The solid was collected by suction filtration, washed with acetonitrile and dried in-vacuo. Yield: 490 mg, 88%, mp 255.9–256.8° C. $^1$H NMR (D$_2$O/DMSO-$d_6$/NaOD/300 MHz) 7.93 (d, 2H), 7.09 (s, 4H), 7.00 (d, 2H), 4.42 (m, 1H), 2.26 (br m, 2H,) 2.12 (br m, 2H), 1.92 (s, 3H), 1.68 (br m, 2H), 1.57 (br m, 2H). ESLRMS m/z 369 (M+H).

EXAMPLE 41

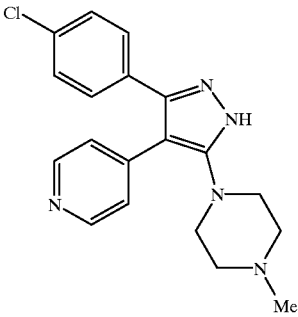

Step 1. A mixture of the dithietane from Example 2 (78.3 g, 0.24 mol) and 1-methylpiperazine (75.0 g, 0.73 mol) in 800 mL of toluene was heated to reflux for 2 h. Solvent and excess 1-methylpiperazine was removed under vacuum and the residue was triturated with a mixture was ethyl acetate and ether (1:3) to give 53.0 g of product as yellow crystals, 60%, mp 149–151° C.

Anal. Calc'd. for $C_{19}H_{20}ClN_3OS$: C, 61.03; H, 5.39; N, 11.24. Found: C, 60.74; H, 5.35; N, 11.14.

Step 2. To a suspension of the product from Step 1 (52.0 g, 0.14 mol) in 500 mL of dry tetrahydrofuran was added anhydrous hydrazine (8.9 g, 0.28 mol) dropwise. The reaction mixture was stirred at room temperature for 16 h. The pale yellow precipitate was filtered and recrystallized from hot methanol to give 30.2 g of the title compound as a white powder, 60%, mp 267–268° C.

Anal. Calc'd. for $C_{19}H_{20}ClN_5$: C, 64.49; H, 5.70; N, 19.79. Found: C, 64.89; H, 5.55; N, 19.99.

EXAMPLE 42

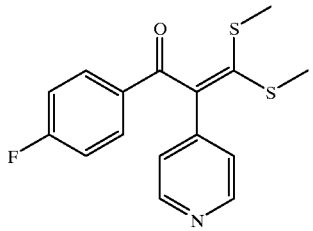

To 1-(4-fluorophenyl)-2-(4-pyridyl)ethanone (1.0 g, 4.7 mmol), in anhydrous THF (10 mL) was added a solution of 1M potassium t-butoxide in THF (10 mL, 10 mmol). The reaction mixture was stirred for 15 minutes at room temperature, then carbon disulfide (0.31 mL, 5.1 mmol) was added. After several minutes, methyl iodide (0.64 mL, 10.3 mmol) was added and the reaction allowed to stir for 4 hours. The reaction mixture was diluted with saturated sodium bicarbonate solution (25 mL) and extracted twice with ethyl acetate (35 mL). The combined ethyl acetate layers were washed with water (25 mL) and brine (25 mL). The organic solution was dried ($MgSO_4$), filtered and concentrated to an orange oil. The oil solidified on standing to afford 1.4 g, 94%, of the expected product mp 80.2–82.1° C. $^1$H-NMR ($CDCl_3$/300 MHz) 8.59 (d, 2H), 7.96 (m, 2H), 7.38 (m, 2H), 7.14 (m, 2H), 2.33 (s, 3H), 2.23 (s, 3H).

Anal. Calc'd for $C_{16}H_{14}FNOS_2$: C, 60.16; H, 4.42; N, 4.39; S, 20.08. Found: C, 59.89; H, 4.09; N, 4.31; S, 20.14.

EXAMPLE 43

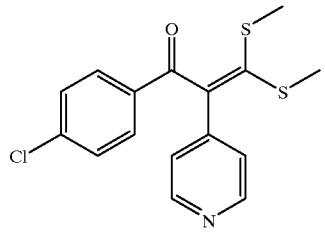

The product was prepared in a manner analogous to Example 42 starting from 1-(4-chlorophenyl)-2-(4-pyridyl)ethanone. Crude yield; 100%, mp 87.6–88.2 ° C. $^1$H-NMR ($CDCl_3$/300 MHz) 8.60 (d, 2H), 7.87 (d, 2H), 7.44 (d, 2H), 7.37 (m, 2H), 2.33 (s, 3H), 2.22 (s, 3H). ESHRMS m/z 336.0297 (M+H, $C_{16}H_{14}ClNOS_2$ requires 336.0283).

Anal. Calc'd for $C_{16}H_{14}ClNOS_2$: C, 57.22; H, 4.20; N, 4.17. Found: C, 57.44; H, 3.97; N, 4.04.

EXAMPLE 44

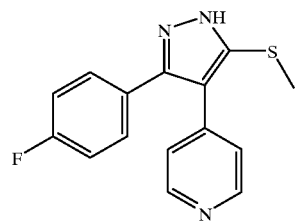

To the product of Example 42 (1.4 g, 4.4 mmol) in ethanol (15 mL) was added 1M hydrazine in acetic acid (5 mL, 5 mmol). The reaction was stirred at room temperature for 18 hours. No reaction had occurred, so additional hydrazine hydrate (1.08 mL, 22 mmol) was added and the reaction heated to reflux for 6 hours. The product began to precipitate from the reaction mixture. The reaction was cooled to room temperature and water was added to precipitate the product. The solid was collected by suction filtration and air dried to afford the crude desired pyrazole, 675 mg, 53%. The product was recrystallized from ethanol, 494 mg, mp 249.9–249.9° C. $^1$H-NMR (DMSO-$d_6$/300 MHz) 13.51 (br s, 1H), 8.50 (d, 2H), 7.34 (m, 2H), 7.23 (m, 2H), 7.16 (m, 2H), 2.43 (s, 3H). ESHRMS m/z 286.0807 (M+H, $C_{15}H_{13}FN_3S$ requires 286.0814).

Anal. Calc'd for $C_{15}H_{12}FN_3S$: C, 63.14; H, 4.24; N, 14.73. Found: C, 63.01; H, 4.43; N, 14.81.

EXAMPLE 45

The product was made in an analogous manner to Example 44 starting with the product of Example 43. Yield; 750 mg, 33%, mp 250.2–250.2° C. $^1$H NMR (DMSO-$d_6$/300 MHz) 13.57 (br s, 1H), 8.51 (m, 2H), 7.45 (br s, 2H), 7.32 (m, 2H), 7.17 (m, 2H), 2.43 (s, 3H). ESHRMS m/z 302.0537 (M+H, $C_{15}H_{13}ClN_3S$ requires 302.0518).

Anal. Calc'd for $C_{15}H_{12}ClN_3S$: C, 59.70; H, 4.01; N, 13.92. Found: C, 59.56; H, 3.96; N, 13.96.

EXAMPLE 46

To the product of Example 44 (150 mg 0.52 mmol) in ethanol (15 mL) was added ammonium persulfate (450 mg, 1.97 mmol). The reaction mixture was stirred at ambient temperature. After several hours an additional amount of ammonium persulfate (450 mg) was added. The reaction mixture was monitored by TLC (silica) using 5% methanol in dichloromethane as the eluting solvent. When the starting material had been consumed, the reaction mixture was quenched with saturated sodium bicarbonate (25 mL) and extracted with ethyl acetate (2×25 mL). The ethyl acetate layers were combined, washed with brine (25 mL) and dried (MgSO$_4$). Filtration and concentration produced a white solid. The solid was triturated with diethyl ether, collected by suction filtration, and air dried to provide 150 mg, 96%, mp 262.9–262.9° C. of the desired sulfoxide. $^1$H NMR (DMSO-d$_6$/300 MHz) 14.22 (br s, 1H), 8.56 (d, 2H), 7.42–7.23 (br m, 6H), 2.94 (s, 3H).

Anal. Calc'd for C$_{15}$H$_{12}$FN$_3$OS 0.25 H$_2$O: C, 58.91; H, 4.12; N, 13.74. Found: C, 58.88; H, 4.17; N, 13.39.

EXAMPLE 47

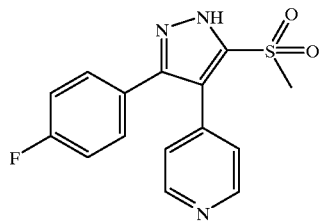

To the product of Example 44 (285 mg, 1 mmol) in ethanol (10 mL) was added potassium peroxymonosulfate (2.45 g, 4 mmol) and water (5 mL). The reaction mixture was stirred at ambient temperature. After 6 hours the reaction mixture was diluted with water (20 mL) and extracted with ethyl acetate (2×30 mL). The ethyl acetate layers were combined, washed with brine (25 mL) and dried (MgSO$_4$). The ethyl acetate did not efficiently extract the product from the aqueous phase, so the aqueous layer was saturated with sodium chloride and extracted with acetonitrile (50 mL). The acetonitrile solution was dried (MgSO$_4$), filtered, and combined with the filtered ethyl acetate solution. The solvents were evaporated and the resulting solid was triturated with a small amount of acetonitrile, collected by suction filtration, and air dried to afford 203 mg, 64, %, mp 297.1–>300° C. $^1$H NMR (DMSO-d$_6$/300 MHz) 14.37 (br s, 1H), 8.54 (m, 2H), 7.29 (m, 6H), 3.26 (s, 3H).

Anal. Calc'd for C$_{15}$H$_{12}$FN$_3$O$_2$S: C, 56.77; H, 3.81; N, 13.24. Found: C, 56.52; H, 4.03; N, 13.11.

EXAMPLE 48

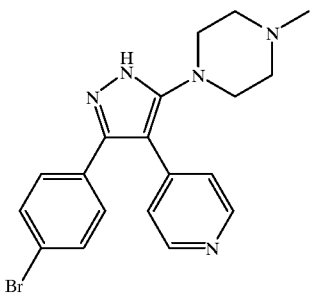

The product was prepared in a similar manner to Example 1 starting from methyl 4-bromobenzoate. Obtained a white solid, mp 270.2–270.7° C. $^1$H NMR (DMSO-d$_6$/300 MHz) 12.7 (br s, 1H), 8.47 (m, 2H), 7.57 (m, 2H), 7.21 (m, 2H), 2.85 (m, 4H), 2.34 (m, 4H) 2.15 (s, 3H). ESHRMS 398.0993 (M+H, C$_{19}$H$_{21}$BrN$_5$ requires 398.0980).

EXAMPLE 49

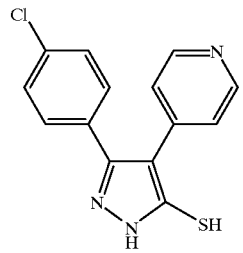

The product from Example 2 (50 g, 0.156 mol) and anhydrous hydrazine (25 mL, 0.8 mol) were heated to reflux in ethanol for 5 hours. The contents were allowed to cool whereupon a precipitate formed that was isolated by filtration. The solid was air dried to afford the desired product as a yellow-orange solid (21.8 g). The filtrate was diluted with water (200 mL) and a second crop was obtained as a yellow-orange solid (18.0 g). The pH of the filtrate was adjusted to pH 8 with 3N HCl and the precipitated solid filtered to give an additional crop of the desired product as a yellow-orange solid (2.0 g). The combined crops afforded the desired pyrazole in 93% yield, mp 266.3–268.9° C. $^1$H NMR (DMSO-d$_6$) 13.80 (br, 1H); 12.20 (br s, 1H); 8.32 (s, 4H); 7.50–7.30 (m, 4H). ESHRMS m/z 288.0358 (M+H, C$_{14}$H$_{11}$ClN$_3$S requires 288.0362).

Anal. Calc'd for: C$_{14}$H$_{10}$ClN$_3$S (0.4 H$_2$O): C, 57.01; H, 3.69; N, 14.25. Found: C, 56.95; H, 3.50 N, 14.14.

EXAMPLE 50

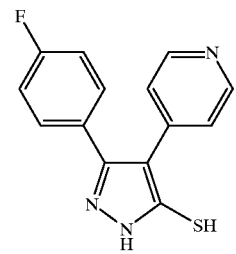

The above pyrazole was prepared by the method outlined in Example 49 mp 261.3–263.9° C. $^1$H NMR (DMSO-d$_6$) 11.55 (br s, 1H); 8.25–8.13 (m, 2H); 7.61–7.50 (m, 2H); 7.36–7.20 (m, 2H); 7.19–7.05 (m, 2H). ESHRMS m/z 272.0691 (M+H, C$_{14}$H$_{11}$FN$_3$S requires 272.0657).

Anal. Calc'd for: C$_{14}$H$_{10}$FN$_3$S (0.25 H$_2$O): C, 60.97; H, 3.84; N, 15.24. Found: C, 61.05; H, 3.64 N, 15.12.

EXAMPLE 51

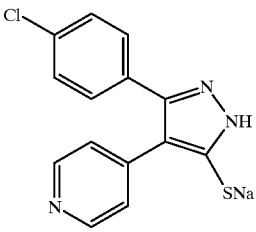

To the product from Example 49 (100 mg, 0.35 mmol) in methanol (2 mL) was added 0.5 M sodium methoxide (0.7 ml, 0.35 mmol). Contents were stirred for 15 minutes and filtered to remove a precipitate. The filtrate was concentrated in vacuo, dissolved in water and concentrated in vacuo leaving the desired product as a white solid. $^1$H NMR (DMSO-d$_6$) 11.60 (br s, 1H); 8.20 (d, 2H); 7.60–7.50 (m, 2H); 7.40– 7.20 (m, 4H).

Anal. Calc'd for: $C_{14}H_9ClN_3NaS$ (2.5 H$_2$O): C, 47.40; H, 3.98; N, 11.84. Found: C, 47.39; H, 3.33; N, 11.50.

EXAMPLE 52

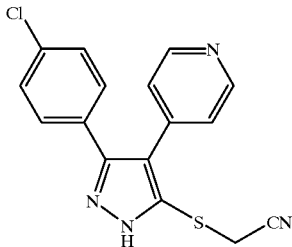

To the material prepared in Example 49 (584 mg, 2.0 mmol) and bromoacetonitrile (140 ul, 2.0 mmol) in DMF (5 mL) was added anhydrous potassium carbonate (276 mg, 2.0 mmol). Contents were stirred overnight, then partitioned between EtOAc and H$_2$O. The EtOAc layer was dried over MgSO$_4$ and concentrated in vacuo leaving a tan solid. The solid was triturated with MeOH and filtered to give the desired product as a off-white solid, 369 mg, 56%, mp 230.0–230.5° C. $^1$H NMR (DMSO-d$_6$) 13.90 (br s, 1H); 8.58 (d, 2H); 7.60–7.13 (m, 6H); 4.10 (s, 2H). ESHRMS m/z 327.0482 (M+H, $C_{16}H_{11}ClN_4S$ requires 327.0471).

Anal. Calc'd for: $C_{16}H_{11}ClN_4S$(0.3 H$_2$O): C, 57.85, H, 3.52; N, 16.87. Found: C, 57.88; H, 3.31; N, 16.77.

EXAMPLE 53

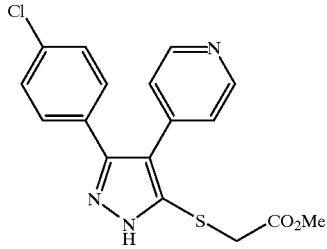

Prepared by the method described in Example 52, using methyl chloroacetate. When the contents were partitioned between EtOAc and H$_2$O, an insoluble solid was filtered to give the desired product as a white solid 2.16 g. A second crop, 1.68 g, of the desired product gave a total yield of 61%, mp 192.8–195.2° C. $^1$H NMR (DMSO-d$_6$+approx. 10% TFA) 9.80 (d, 2H); 7.80 (d, 2H); 7.52–7.34 (m, 4H); 3.92 (s, 2H); 3.57 (s, 3H). ESHRMS m/z 36.05735 (M+H, $C_{17}H_{15}ClN_3O_2$ requires 360.05732).

Anal. Calc'd for: $C_{17}H_{14}ClN_3O_2$ (0.25 H$_2$O): C, 56.05, H, 4.01; N, 11.53. Found: C, 56.10; H, 3.72; N, 11.51.

EXAMPLE 54

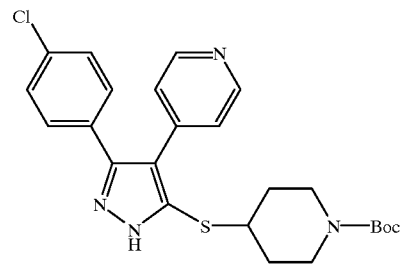

The above compound was prepared by heating the product of Example 49 (1.2 g, 4.2 mmol), potassium carbonate (630 mg , 4.6 mmol), N-boc-4-bromopiperidine (1.2 g, 4.5 mmol) were heated in DMF (15 mL) at 105 C for 3 hours. Contents were allowed to cool and partitioned between EtOAc and water. The EtOAc layer was dried over MgSO$_4$ and concentrated in vacuo. The residue was triturated with EtOAc and filtered to give the desired as a white solid 1.20 g, 61%, mp 220.9–221.0° C. $^1$H NMR (DMSO-d$_6$) 13.70 (br, 1H); 8.60–8.50 (m, 2H); 7.58–7.10 (m, 6H); 3.80–3.60 (m, 2H); 3.40–3.20 (m, 1H); 3.00–2.63 (m, 2H); 2.00–1.53 (m, 2H); 1.50–1.05 (m, 2H); 1.40 (s, 9H). FABHRMS m/z 471.1605 (M+H, $C_{24}H_{28}ClN_4OS$ requires 471.1622).

Anal. Calc'd for: $C_{24}H_{27}ClN_4OS$ (0.5 H$_2$O): C, 60.05; H, 5.88; N, 11.67. Found: C, 60.04; H. 5.57; N, 11.31.

EXAMPLE 55

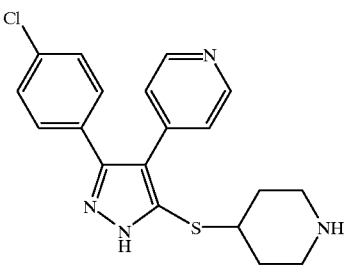

The product from Example 54 (5.0 g, 11 mmol), and TFA (30 mL) were mixed in CH$_2$Cl$_2$ (50 mL) and stirred overnight. Contents were concentrated in vacuo leaving a pale yellow oil which was dissolved in water. The pH was adjusted with 2.5 N NaOH to pH 9, causing a white solid to form that was isolated by filtration to provide the desired product as a white solid, 3.7 g, 93%, mp 211.1–211.2° C. $^1$H NMR (DMSO-d$_6$) 13.80 (br, 1H); 8.55 (1, 2H); 8.40 (br, 1H); 7.50–7.15 (m, 6H); 3.50–3.00 (m, 3H); 3.00–2.80 (m, 2H); 2.05–1.80 (m, 2H); 1.65–1.42 (m, 2H). ESHRMS m/z 371.1103 (M+H, $C_{19}H_{20}ClN_4S$ requires 371.1097).

Anal. Calc'd for: $C_{19}H_{19}ClN_4S$ (H$_2$O): C, 58.68; H, 5.44; N, 14.41. Found: C, 58.86; H, 5.28; N, 14.25.

EXAMPLE 56

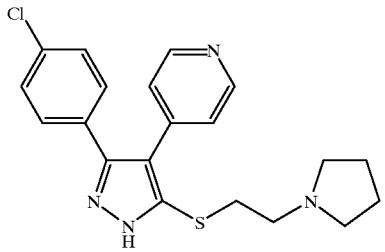

To 1-(2-chloroethyl)pyrrolidine hydrochloride (306 mg, 1.8 mmol) in methanol (10 mL) was added 0.5 M sodium methoxide (7.0 mL, 3.6 mmol). Contents were stirred 10 minutes and then the material from Example 49 (500 mg, 1.8 mmol) were added. Contents were heated to reflux 1 hour, allowed to cool and partitioned between EtOAc and $H_2O$. The EtOAc layer was dried over $MgSO_4$ and concentrated in vacuo leaving a light amber solid. The solid was recrystallized from MeOH (15 mL) to give the desired product as a white solid (213 mg, 33% yield). mp 189.9–190.1° C. $^1H$ NMR (DMSO-$d_6$) 13.65 (br, 1H); 8.52 (d, 2H); 7.42 (d, 2H); 7.38–7.10 (m, 4H); 3.10–2.93 (m, 2H); 2.63–2.51 (m, 2H); 2.38 (br, s, 4H); 1.70–1.52 (m, 4H). ESHRMS m/z 385.1262 (M+H, $C_{20}H_{22}ClN_4$ requires 385.1254).

Anal. Calc'd for: $C_{20}H_{21}ClN_4$: C, 62.41, H, 5.50; N, 14.56. Found C, 62.22; H, 5.62; N, 14.48.

EXAMPLE 57

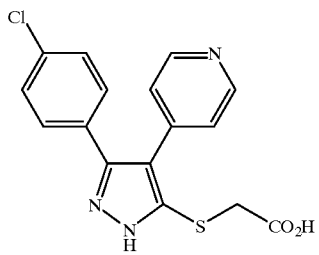

Method A. The material prepared in Example 53 (1.3 g, 3.6 mmol) in methanol (10 mL), 2.5N sodium hydroxide (4 mL) and water (10 mL) were stirred overnight. The contents were concentrated in vacua to remove the methanol and the aqueous solution left was made acidic to pH 6 with 3N HCl, precipitating a solid. The solid was extracted into EtOAc, dried over $MgSO_4$ and concentrated in vacuo leaving light tan crystals, 205 mg. Brine was added to the aqueous layer precipitating additional solid that was filtered to give more desired product as a light tan powder, 529 mg, the total yield was 61%. $^1H$ NMR (DMSO-d6+10% TFA) 8.80 (d, 2H); 7.83 (d, 2H); 7.55–7.35 (m, 4H); 3.87 (s, 2H).

Method B. The product from Example 53 (3.8 g, 11 mmol) and 3N HCl (30 mL) were heated to reflux for 3 hours. Contents were allowed to cool and concentrated in vacuo. The residue was mixed with $CH_3CN$ (50 mL). Upon standing overnight, pale yellow crystals grew that were isolated by filtration to afford the desired product as the HCl salt 2.9 g, 69%. $^1H$ NMR (DMSO-$d_6$) 8.79 (d, 2H); 7.75 (d, 2H); 7.51–7.38 (m, 4H); 3.88 (s, 2H). ESHRMS m/z 346.0435 (M+H, $C_{17}H_{13}ClN_4OS$ requires 346.0417).

Anal. Calc'd for: $C_{17}H_{12}ClN_4OS$ (HCl, 0.5 $H_2O$): C, 49.12; H, 3.61; N, 10.74. Found: C, 49.36; H, 3.48; N, 10.72.

EXAMPLE 58

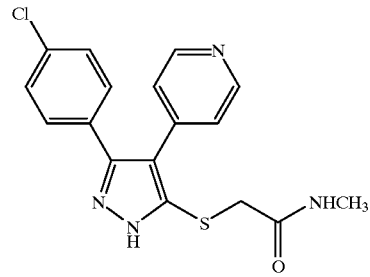

The material prepared in Example 53 (400 mg, 11 mmol) and a 2M solution of methylamine in THF (25 mL) were heated to reflux for 3 hours. The reaction was stirred overnight at room temperature and then filtered to afford the desired product as a light amber solid, 335 mg, 85%, mp 284.0–288.4° C. $^1H$ NMR (DMSO-$d_6$) 13.58 (br, 1H); 8.60–8.45 (m, 2H); 7.98 (br s, 1H); 7.55–7.12 (m, 6H); 3.60 (s, 2H); 2.46 (s, 3H). ESHRMS m/z 359.0733 (M+H, $C_{17}H_{16}ClN_4OS$ requires 359.0745).

Anal. Calc'd for: $C_{17}H_{15}ClN_4OS$: C, 56.90; H, 4.21; N, 15.61. Found: C, 56.74 H, 4.11; N, 15.17.

EXAMPLE 59

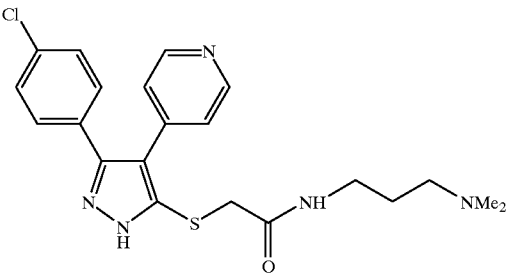

The material prepared in Example 53 (415 mg, 12 mmol) and N,N-dimethylaminopropylamine were heated to reflux in methanol (25 mL) for 3 hours. The contents were stirred overnight at room temperature and then concentrated in vacuo to afford a solid. The solid was triturated with EtOAc and filtered to give the desired product as a white solid. 256 mg, 50%, mp 168.8–169.5° C. $^1H$ NMR (DMSO-$d_6$) 13.80 (br, 1H); 8.55–8.50 (m, 2H); 8.02 (t, 1H); 7.50–7.40 (m, 6H); 3.61 (s, 2H); 3.30–2.98 (m, 2H); 2.14–2.10 (m, 2H); 2.04 (s, 6H); 1.50–1.40 (m, 2H). FABHRMS m/z 430.1472 (M+H, $C_{21}H_{25}ClN_5OS$ requires 430.1468).

Anal. Calc'd for: $C_{21}H_{24}ClN_5OS$ (0.5 $H_2O$): C, 57.46; H, 5.74; N, 15.95. Found: C, 57.71; H, 5.56; N, 16.12.

EXAMPLE 60

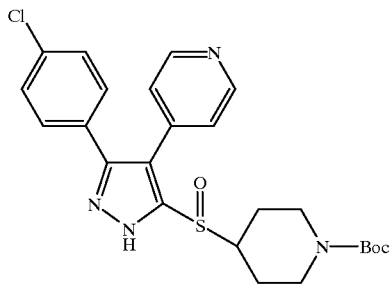

To the material prepared in Example 54 (1.0 g, 2.1 mmol) in $CH_2Cl_2$ (25 mL) was added 3-chloroperbenzoic acid (425 mg, 2.1 mmol). The reaction was stirred 15 minutes and then chromatographed on silica gel (20 g) eluting with EtOAc. The desired product crystallized from the collected fractions and the product was isolated by filtration and air dried to give 958 mg, 93% mp 215.8–215.9° C. $^1$H NMR (DMSO-$_6$) 14.34 (br s, 1H); 8.57–8.54 (m, 2H); 7.51–7.25 (m, 6H); 4.00–3.82 (m, 2H); 3.60–3.40 (m, 1H); 2.85–2.70 (m, 2H); 2.10–1.95 (m, 1H); 1.56–1.10 (m, 3H); 1.36 (s, 9H). ESHRMS m/z 437.1580 (M+H, $C_{24}H_{28}ClN_4O_3S$ requires 487.1571).

Anal. Calc'd for: $C_{24}H_{27}ClN_4O_3S$: C, 59.19; H, 5.59; N, 11.50. Found: C, 59.00; H, 5.76; N, 11.46.

EXAMPLE 61

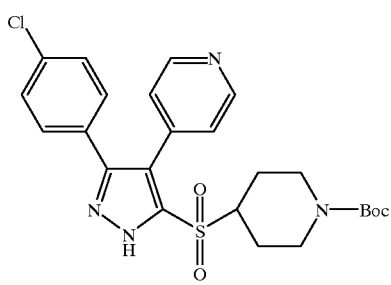

To the material prepared in Example 60 (320 mg, 0.68 mmol) in EtOH (5 mL) was added an aqueous solution of potassium peroxymonosulfate (420 mg, 0.68 mmol). Contents were stirred for 2 hours and extracted into EtOAc. The extracts were dried over MgSO$_4$ and concentrated in vacuo leaving a white solid. The solid was triturated with methanol and filtered to give the desired as a white solid, 90 mg, 26%, mp 228.0–230.8° C. $^1$H NMR (DMSO-d$_6$) 8.61 (d, 2H); 7.48 (d, 2H); 7.31–7.20 (m, 4H); 4.05–3.90 (m, 2H); 3.54–3.35 (m, 1H); 2.85–2.60 (m, 2H); 1.92–1.80 (m, 2H); 1.48–1.25 (m, 2H); 1.32 (s, 9H). ESHRMS m/z 503.1541 (M+H, $C_{24}H_{28}ClN_4O_4S$ requires 503.1520).

Anal. Calc'd for: $C_{24}H_{27}ClN_4O_4S$ (H$_2$O): C, 56.30; H, 5.51; N, 10.94. Found: C, 56.41; H, 5.78; N, 10.54.

EXAMPLE 62

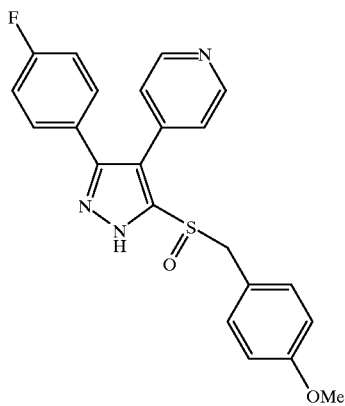

The product from Example 48 was converted to the corresponding sulfoxide by the procedure described Example 60. The crude product was purified by flash chromatography, the solid thus obtained was recrystallized from acetonitrile to give the desired product as white crystals, 64 mg, 33%, mp 189.5–189.5° C. $^1$H NMR (DMSO-d$_6$) 14.28 (br s, 1H); 8.50 (d, 2H); 7.40–7.20 (m, 4H); 7.20–7.05 (m, 4H); 6.85 (d, 2H); 4.41 (s, 2H); 3.70 (s, 3H). ESHRMS m/z 408.1168 (M+H, $C_{22}H_{19}FN_3O_2S$ requires 408.1182).

Anal. Calc'd for: $C_{22}H_{18}FN_3O_2S$: C, 64.85; H, 4.45; N, 10.31. Found: C, 64.44; H, 4.34; N, 10.70.

EXAMPLE 63

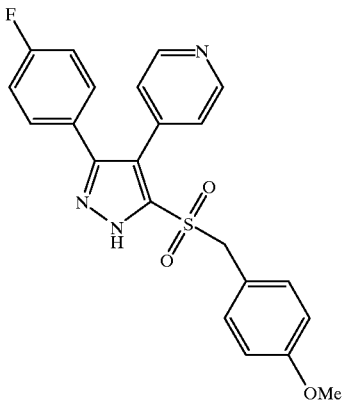

To the material prepared in Example 62 (1.2 g, 2.5 mmol) in CH$_2$Cl$_2$ (50 mL) was added 3-chloroperbenzoic acid (1.0 g, 5.0 mmol). Contents were stirred 1.5 hours and then filtered to remove a white solid (620 mg). The filtrate was concentrated and the residue chromatographed on silica gel (20 g) eluting with EtOAc to give the desired product as a white solid, 98 mg, 9%, mp 241.9–242.0° C. $^1$H NMR (DMSO-d$_6$) 8.48–8.40 (m, 2H); 7.33–6.80 (m, 10H); 4.55 (s, 2H); 3.72 (s, 3H). ESHRMS m/z 424.1143 (M+H, $C_{22}H_{19}FN_3O_3S$ requires 424.1131).

Anal. Calc'd for: $C_{22}H_{18}FN_3O_3S$: C, 62.40; 11,4.28; N, 9.92. Found: C, 62.14; H, 4.42;, N, 9.68.

EXAMPLE 64

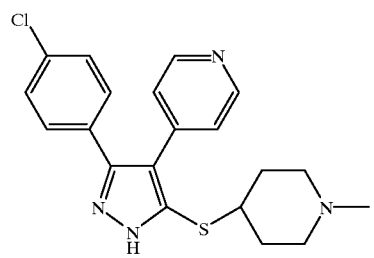

The product from Example 54 (5.0 g, 0.01 mol) and formic acid (96%, 7 mL) were heated at 100° C. for 1 hour. Contents were allowed to cool to about 50° C. and added formaldehyde (37%, 13 mL). The reaction was heated at 80° C. for an additional 2 hours, and then allowed to cool, diluted with water (200 mL) and made basic to pH 11 with 2.5N NaOH whereupon a precipitate formed. The solid was isolated by filtration and recrystallized from methanol to give the desired product as a white solid, 174 mg, 33%, mp 227.7–227.7° C. $^1$H NMR (DMSO-d$_6$) 13.70 (br s, 1H); 8.56–8.48 (m, 2H); 7.50–7.15 (m, 6H); 3.10–2.92 (m, 1H); 2.63–2.50 (m, 2H); 2.05 (s, 3H); 1.95–1.65 (m, 4H); 1.50–1.30 (m, 2H). ESHRMS m/z 385.1233 (M+H, $C_{20}H_{22}ClN_4S$ requires 385.1254).

Anal. Calc'd for: $C_{20}H_{21}ClN_4S$: C, 62.41; H, 5.50; N, 14.56. Found: C, 62.40; H, 5.80; N, 14.61.

EXAMPLE 65

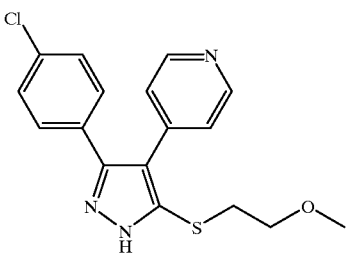

The above compound was prepared from Example 49 according to the procedure described in Example 54 using bromoethyl methyl ether except that the contents were heated at 70° C. for 1 hour before partitioning between EtOAc and H$_2$O. The crude was recrystallized from MeOH/EtOAc to give the desired product as a white solid, 210 mg, 35%, mp 189.2–190.2° C. $^1$H NMR (DMSO-d$_6$) 8.60–8.45 (m, 2H); 7.60–7.10 (m, 6H); 3.60–2.85 (m, 7H). ESHRMS m/z 346.0799) M+H, C$_{17}$H$_{17}$ClN$_3$OS requires 346.0781).

Anal. Calc'd for: C$_{17}$H$_{16}$ClN$_3$OS (H$_2$O): C, 58.73; H, 4.70; N, 12.09. Found: C, 58.67; H, 4.86; N, 12.03.

EXAMPLE 66

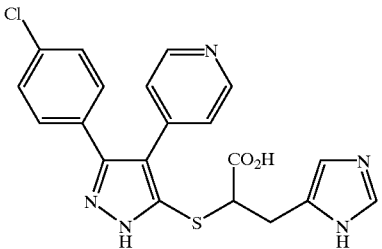

The above compound was prepared from Example 49 according to the procedure described in Example 54 using 2-chloromethylbenzimidazole except that the contents were heated at 70° C. for 1 hour before partitioning between EtOAc and H$_2$O. An insoluble solid was filtered from the two layers and triturated with MeOH to give the desired product as a light amber solid, 292 mg, 40%, mp 257.7–257.7° C. $^1$H NMR (DMSO-d$_6$) 13.75 (br s, 1H); 12.30 (br s, 1H); 8.55–8.30 (m, 2H); 7.65–6.90 (m, 10H); 4.40 (br s, 2H). FABHRMS m/z 418.0895 (M+H, C$_{22}$H$_{17}$ClN$_5$ requires 418.0893).

Anal. Calc'd for: C$_{22}$H$_{16}$ClN$_5$ (0.75 H$_2$O): C, 61.25; H, 4.09; N, 16.23. Found: C, 61.27; H, 3.90; N, 15.92.

EXAMPLE 67

The above compound was prepared from Example 49 according to the procedure described in Example 54 using D,L-alpha-bromo-beta-(4-imidazolyl)propionic acid except that the contents were heated at 70° C. for 1 hour. The contents contained an insoluble solid which was diluted with water and the pH was adjusted with 3N HCl to pH 7. Contents were filtered and triturated with MeOH to give the desired product as a white solid, 1.5 g, 81%, mp 163.0–165.5° C. $^1$H NMR (DMSO-d$_6$+approx. 10% TFA) 8.92 (d, 1H); 8.83–8.75 (m, 2H); 7.80 (d, 2H); 7.55–7.30 (m, 5H); 4.20–4.05 (m, 1H); 3.25–3.00 (m, 2H). ESHRMS m/z 426.0799 (M+H, C$_{20}$H$_{17}$ClN$_5$O$_2$S requires 426.0791).

Anal. Calc'd for: C$_{20}$H$_{16}$ClN$_5$O$_2$S (1.8 H$_2$O): C, 52.41 H, 4.31; N, 15.28. Found: C, 52.68; H, 4.58; N, 15.37.

EXAMPLE 68

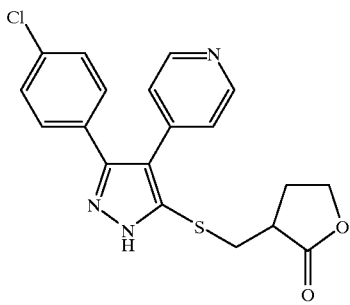

The above compound was prepared from Example 49 (264 mg, 0.9 mmol) according to the procedure described in Example 54 and alpha-methylenebutyrolactone (0.08 mL, 0.9 mmol) in EtOH was added a drop of triethylamine. Contents were stirred overnight and the resulting solid was filtered and triturated with MeOH to give the desired product as a pale yellow solid, 181 mg, 51%, mp 224.2–225.9° C. $^1$H NMR DMSO-d$_6$+approx. 10% TFA) 8.80 (d, 2H); 7.80 (d, 2H); 7.53–7.33 (m, 4H); 4.30–4.05 (m, 2H); 3.50–3.40 (m, 1H); 3.15–2.90 (m, 2H); 2.32–2.20 (m, 1H) 2.10–1.90 (m, 1H). ESHRMS m/z 386.0760 (M+H, C$_{19}$H$_{17}$ClN$_3$O$_2$S requires 386.0730).

Anal. Calc'd for: C$_{19}$H$_{16}$ClN$_3$O$_2$S: C, 59.14 H, 4.18; N, 10.89. Found: C, 58.97; H, 4.21; N, 10.96.

EXAMPLE 69

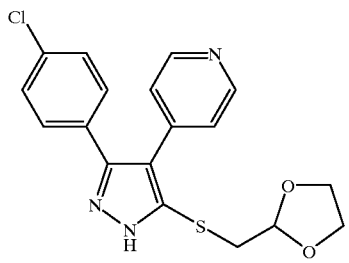

The above compound was prepared from Example 49 according to the procedure described in Example 54 using 2-bromomethyl-1,3-dioxolane except that the contents were heated at 80° C. for 2 hours. The reaction was diluted with water and filtered to give a white solid, 502 mg. The solid was recrystallized from EtOH to give the desired product as off-white crystals, 280 mg, 43%, mp 197.0–198.2° C. $^1$H NMR (DMSO-d$_6$) 13.60 (br s, 1H); 8.60–8.45 (m, 2H); 7.60–7.10 (m, 6H); 5.15–4.85 (m, 1H); 3.95–3.62 (m, 4H); 3.40–2.95 (m, 2H). ESHRMS m/z 374.0741 (M+H, C$_{18}$H$_{17}$ClN$_3$O$_2$S requires 374.07 30).

Anal. Calc'd for: $C_{18}H_{16}ClN_3O_2S$: C, 57.83 H, 4.31; N, 11.24. Found: C, 57.69; H, 4.41; N, 11.15.

EXAMPLE 70

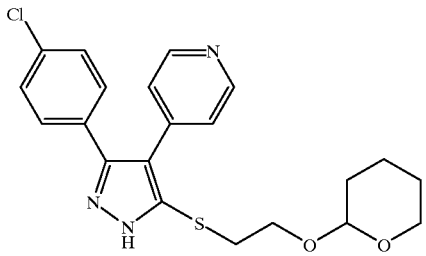

The above compound was prepared from Example 53 according to the procedure described in Example 54 using 2-(2-bromoethoxy)tetrahydro-2H-pyran except that the contents were heated at 80° C. for 4 hours. Contents were allowed to cool and partitioned between EtOAc and water. The EtOAc layer was dried over $MgSO_4$ and concentrated in vacuo leaving a solid, 737 mg. The solid was recrystallized from EtOH to give the desired product as pale yellow crystals, 281 mg, 39%, mp 163.2–163.5° C. $^1$H NMR (DMSO-$d_6$) 13.80–13.70 (m, 1H), 8.60–8.42 (br s, 1H); 7.60–7.10 (m, 6H); 4.60–4.30 (m, 1H); 3.90–2.90 (m, 6H); 1.70–1.20 (m, 6H). ESHRMS m/z 416.1200 (M+H, $C_{21}H_{23}ClN_3O_2S$ requires 416.1198).

Anal. Calc'd for: $C_{21}H_{22}ClN_3O_2S$: C, 60.64 H, 5.33; N, 10.10. Found: C, 60.49; H, 5.71; N, 9.96.

EXAMPLE 71

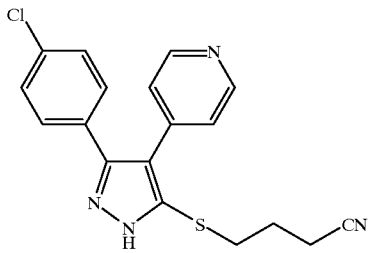

The above compound was prepared from Example 49 according to the procedure described in Example 54 using 4-bromobutyronitrile except that the contents were heated at 55° C. for 1 hour. Contents were diluted with water (75 mL) and filtered to give a white solid, 567 mg. The solid was recrystallized from MeOH to give the desired product as white crystals, 333 mg, 54%, mp 216.7–216.9° C. $^1$H NMR (DMSO-$d_6$+approx. 10% TFA) 8.80–8.75 (m, 2H); 7.83–7.75 (m, 2H); 7.50–7.35 (m, 4H); 3.10–3.00 (m, 2H); 2.60–2.45 (m, 2H); 1.95–1.80 (m, 2H). ESHRMS m/z 355.0818 (M+H, $C_{18}H_{16}ClN_4SC_{18}H_{16}ClN_4S$ requires 355.0784).

Anal. Calc'd for: $C_{18}H_{15}ClN_4S(0.5\ H_2O)$: C, 59.42 H, 4.43; N, 15.40. Found: C, 59.64; H, 4.11; N, 15.44.

EXAMPLE 72

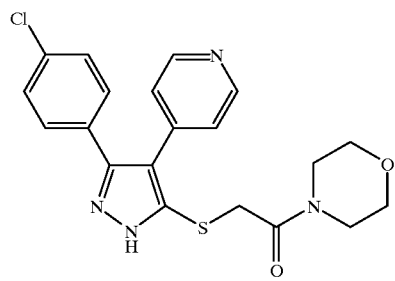

The product from Example 57 (416 mg, 1.1 mmol), morpholine (4 mL), O-benzotriazol-1-yl-N,N,N',N'-tetramethyluronium tetrafluoroborate (481 mg, 1.5 mmol) and DMF (10 mL) were stirred a room temperature overnight. The reaction mixture was diluted with water (75 mL) and the resulting solid isolated by filtration, 363 mg. The crude product was recrystallized from EtOH to give the desired product as a white solid, 219 mg, 48%, mp 215.4–215.5° C. $^1$H NMR (DMSO-$d_6$) 13.70–13.60 (m, 1H); 8.60–8.50 (m, 2H); 7.50–7.10 (m, 6H); 3.93–3.80 (m, 2H); 3.60–3.20 (m, 8H). ESHRMS m/z 415.0995 (M+H, $C_{20}H_{20}ClN_4O_2S$ requires 415.1001).

Anal. Calc'd for: $C_{20}H_{19}ClN_4O_2S$: C, 57.90 H, 4.62; N, 13.50. Found: C, 57.87; H, 4.86; N, 13.53.

EXAMPLE 73

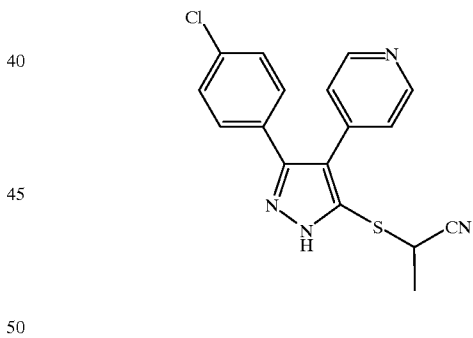

The above compound was prepared from Example 49 according to the procedure described in Example 54 using 2-bromopropionitrile except that the reaction was heated at 70° C. for 1 hour. The reaction solution was diluted with water (75 mL) and filtered to give an off-white solid, 662 mg. The crude product was recrystallized from MeOH to give the desired product as a white solid, 220 mg 37%, mp 211.1–212.8° C. $^1$H NMR (DMSO-$d_6$+approx. 10% TFA) 8.87–8.80 (m, 2H); 7.90–7.80 (m, 2H); 7.55–7.45 (m, 6H); 4.42 (q, 1H); 1.50 (d, 3H). ESHRMS m/z 341.0628 (M+H, $C_{18}H_{14}ClN_4S$ requires 341.0628).

Anal. Calc'd for: $C_{18}H_{13}ClN_4S$: C, 59.91 H, 3.84; N, 16.44. Found: C, 59.64; H, 4.01; N, 16.18.

EXAMPLE 74

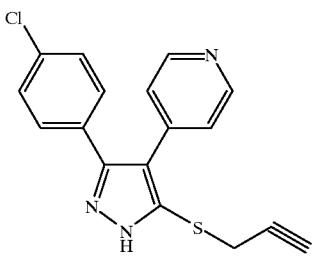

The above compound was prepared from Example 49 according to the procedure described in Example 54 using propargyl bromide. The reaction mixture was diluted with water (75 mL) and filtered o give a pale yellow solid, 577 mg. The solid was triturated with MeOH to give the desired product as a white solid, 388 mg, 68%, mp 212.7–213.2° C. $^1$H NMR (DMSO-$d_6$+approx. 10% TFA) 8.80 (d, J=6.8 Hz, 2H); 7.82 (d, J=6.8 Hz, 2H); 7.50–7.35 (m, 4H); 3.81 (d, J=2.6 Hz, 2H); 3.05 (t, J=2.6 Hz, 1H). ESHRMS m/z 326.0533 (M+H, $C_{17}H_{13}ClN_3S$ requires 326.0519).

Anal. Calc'd for: $C_{17}H_{12}ClN_3S$ (0.2 $H_2O$): C, 61.98 H, 3.79; N, 12.76. Found: C, 61.89; H, 3.45; N, 12.67.

EXAMPLE 75

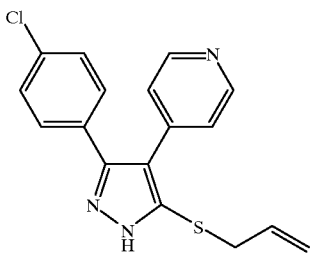

The above compound was prepared from Example 49 according to the procedure described in Example 54 using allyl bromide. The reaction mixture was diluted with water (75 mL) and filtered to give a pale yellow solid, 509 mg. The solid was recrystallized from MeOH to give the desired product as a pale yellow solid, 187 mg, 33%, mp 207.3–208.1° C. $^1$H NMR (DMSO-$d_6$+approx. 10% TFA) 8.80 (d, 2H); 7.80 (d, 2H); 7.50–7.30 (m, 4H); 5.90–5.70 (m, 1H); 5.10–4.95 (m, 2H); 3.62 (d, 2H). ESHRMS m/z 328.0693 (M+H, $C_{17}H_{15}ClN_3S$ requires 328.0675).

Anal. Calc'd for: $C_{17}H_{14}ClN_3S$ (0.1 $H_2O$): C, 61.94 H, 4.34; N, 12.75. Found: C, 61.83; H, 4.21; N, 12.76.

EXAMPLE 76

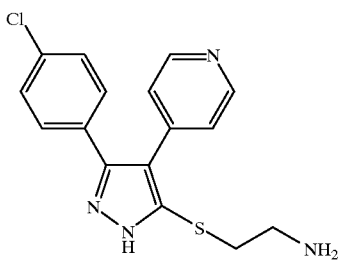

The above compound was prepared from Example 49 according to the procedure described in Example 54 using 2-bromoethylamine hydrochloride except that two equivalents of potassium carbonate were used. The reaction mixture was diluted with water (75 mL) and filtered to give a pale yellow solid, 509 mg. The solid was recrystallized from MeOH to give the desired product as a pale yellow solid, 262 mg, 45%, mp 186.8–187.8° C. $^1$H NMR (DMSO-$d_6$+ approx. 10% TFA) 8.85–8.75 (m, 2H); 8.90 (br s, 2H); 8.85–8.75 (m, 2H); 7.55–7.35 (m, 4H); 3.30–3.00 (m, 4H). ESHRMS m/z 331.0779 (M+H, $C_{16}H_{15}ClN_4S$ requires 331.0784).

Anal. Calc'd for: $C_{16}H_{15}ClN_4S$ (0.5 $H_2O$): C, 56.55; H, 4.75; N, 16.49. Found: C, 56.28; H, 4.38; N, 16.20.

EXAMPLE 77

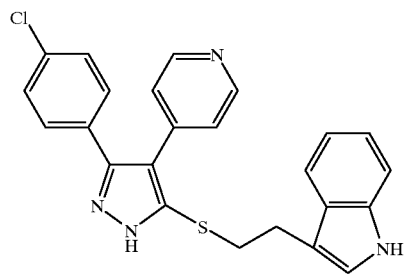

The above compound was prepared from Example 49 according to the procedure described in Example 54 using 3-(2-bromoethyl)indole. The reaction mixture was diluted with water (75 mL) and filtered to give a pale yellow solid, 752 mg. The solid was triturated with MeOH to give the desired product as a white solid, 682 mg, 91%, mp 211.9–213.2° C. $^1$H NMR (DMSO-$d_6$+approx. 10% TFA) 10.80 (s, 1H); 8.72 (d, 2H); 7.71 (d, 2H); 7.55–7.35 (m, 5H); 7.29 (d, 1H); 7.12–6.88 (m, 3H); 3.40–3.30 (m, 2H); 3.05–2.95 (m, 2H). ESHRMS m/z 431.1095 (M+H, $C_{24}H_{20}ClN_4S$ requires 431.1097).

Anal. Calc'd for: $C_{24}H_{19}ClN_4S$(0.15 $H_2O$): C, 66.47 H, 4.49; N, 12.92. Found: C, 66.44; H, 4.51; N, 12.84.

EXAMPLE 78

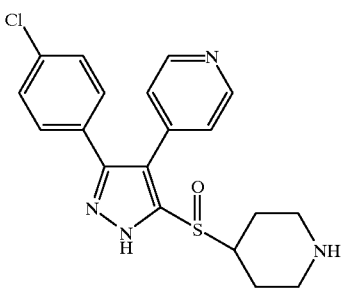

The product from Example 60 (464 mg, 0.95 mmol) and TFA (8 mL) were mixed in $CH_2Cl_2$ (10 mL) and stirred overnight. The reaction mixture was concentrated in vacuo and the residue was partitioned between ether and water. The aqueous layer was made basic to pH 10 with 2.5N NaOH and extracted with EtOAc (2×100 mL). Upon standing overnight, a solid precipitated from the aqueous layer and was filtered to give the desired product as a white solid, 183 mg, 50%, mp 189.1–190.8° C. $^1$H NMR (DMSO-$d_6$+ approx. 10% TFA) 8.85 (d, 2H); 8.80–8.60 (m 1H); 8.45–8.25 (m, 1H); 7.90 (d, 2H); 7.55–7.30 (m, 4H); 3.65–3.20 (m 3H); 3.10–2.80 (m 2H); 2.20–2.00 (m, 1H);

1.90–1.50 (m, 3H). ESHRMS m/z 387.1032 (M+H, $C_{19}H_{20}ClN_4OS$ requires 387.1046).

Anal. Calc'd for: $C_{19}H_{19}ClN_4OS.(2\ H_2O)$: C, 53.96 H, 5.48; N, 13.25. Found: C, 53.75; H, 4.99; N, 13.21.

EXAMPLE 79

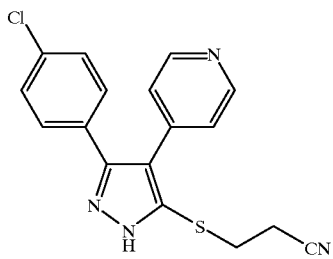

The above compound was prepared from Example 49 according to the procedure described in Example 54 using 3-bromopropionitrile. The reaction mixture was diluted with water (75 mL) and extracted into EtOAc, which was dried over $MgSO_4$ and concentrated in vacuo leaving an orange waxy solid, 523 mg. The solid was dissolved in acetonitrile, filtered through a pad of silica gel and eluted with EtOAc to give a white solid. The solid was triturated with EtOAc and filtered to give the desired product as a white solid, 76 mg, 13%, mp 205.7–206.5° C. $^1$H NMR (DMSO-$d_6$+approx. 10% TFA) 8.80 (d, 2H); 7.80 (d, 2H); 7.55–7.35 (m, 4H); 3.30–3.20 (m, 2H); 2.90–2.80 (m, 2H). ESHRMS m/z 341.0639 (M+H, $C_{14}H_{20}ClN_4S$ requires 341.0628).

Anal. Calc'd for: $C_{14}H_{13}ClN_4S$ (0.25 $H_2O$): C, 59.13 H, 3.94; N, 16.22. Found: C, 59.03; H, 3.93; N, 15.90.

EXAMPLE 80

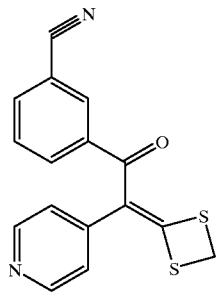

Prepared by the method described in Example 1, steps 1 and 2. mp 168.6–168.7° C. $^1$H NMR (CDCl$_3$/300 MHz) 8.54 (dd, 2H, J=4.6, 1.8 Hz), 7.68–7.62 (m 2H), 7.43–7.39 (m, 1H), 7.33–7.28 (m, 1H), 6.99 (dd, 2H, J=4.4, 1.6 Hz), 4.22 (s, 2H). ESHRMS m/z 311.0330 (M+H, $C_{16}H_{10}N_2OS_2$ requires 311.0313).

Anal. Calc'd. for $C_{16}H_{10}N_2OS_2$: C, 61.91; H, 3.25; N, 9.02. Found: C, 61.45; H, 3.18; N, 8.91.

EXAMPLE 81

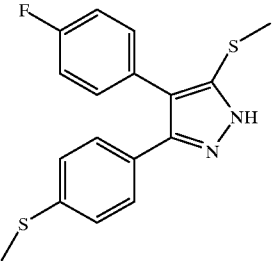

2-(4-flourophenyl)-4-methythiophenylethanone (1.26 g, 4.84 mmol), potassium carbonate (2.04 g 14.5 mmol), carbon disulfide (1.10 g, 14.5 mmol) and dibromomethane (1.10 g, 15.4 mmol) were mixed together in acetone (50 ml) for 12 days. The solution was poured into ethyl acetate (100 mL) and washed with 1N hydrochloric acid. Hexanes (25 mL) were added and the solution was washed with brine (2×100 mL). The organic solution was collected, dried over sodium sulfate and solvent removed at reduced pressure. The product 1 was isolated by crystallization from ethyl acetate and hexanes. 831 mg of yellow crystals were obtained. (49% yield) mp 145.7–145.7° C. $^1$H NMR (CDCl$_3$/300 MHz) 7.19–7.24 (m, 2H), 7.06–7.11 (m, 2H), 6.60–7.30 (m. 4H), 4.11 (s, 2H), 2.42 (s, 3H). HRMS 349.0201 (M+H calcd for $C_{17}H_{14}FOS_3$ 349.0191) .

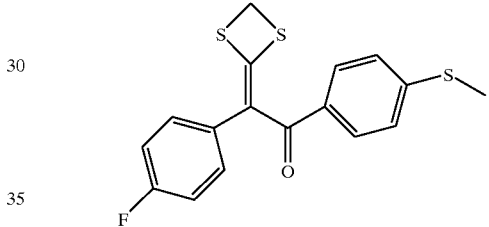

1

The dithiatane (6.13 mg, 1.76 mmol) and anhydrous hydrazine (300 uL) were refluxed in ethanol (10 mL) for 16 hours. The solution was cooled to room temperature and poured into ethyl acetate (50 mL). The solution was extracted with 1 N hydrochloric acid (2×25 mL). Hexanes (10 mL) were added and the solution was extracted with brine (2×25 mL), dried over sodium sulfate, and solvent removed at reduced pressure. The product 2 was isolated by crystallization from dichloromethane and hexanes. 186 mg of yellow crystals were obtained. (32% yield) mp 142.4–143.4° C. $^1$H NMR (CD$_3$OD/400 MHz) 7.18–7.27 (m, 6H), 7.06–7.10 (m, 3H), 2.43 (s, 3H). HRMS 317.0586 (M+H, calcd for $C_{16}H_{14}FN_2S_2$ 317.0582)

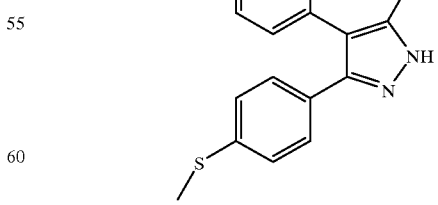

2

The pyrazole 2 (140 mg, 0.44 mmol), potassium carbonate (150 mg, 106 mmol) and iodomethane (71 mg, 0.50 mmol) were stirred in dimethylformamide (5 mL) at room temperature for 16 h. The solution as poured into ethyl acetate (40 mL) and washed with 1N hydrochloric acid (2×40 mL). Hexanes (25 mL) were added and the solution was washed with brine (2×50 mL). The organic solution was collected, dried over sodium sulfate and solvent removed at reduced pressure. The product (22 mg) was isolated as a semi solid by preparative thin layer chromatography. (13% yield) $^1$H NMR (CDCl$_3$/400 MHz) 7.23–7.27 (m, 2H), 7.14–7.22 (m, 2H), 2.46 (s, 3H), 2.41 (s, 3H). HRMS 331.0735 (M+H, C$_{17}$H$_{16}$FN$_2$S$_2$ calcd for 331.0739).

EXAMPLE 82

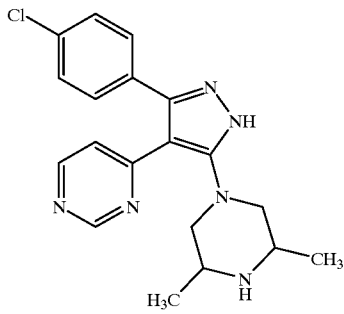

Step 1. Preparation of 1-(4-chlorophenyl )-2-(4-pyrimidyl) ethanone

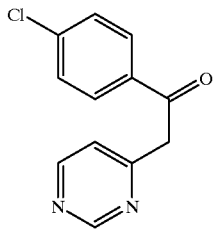

Lithium bis(trimethylsilyl)amide 1.0 M in THF (4.25 L, 4.25 mol) was cooled to −70° C. with stirring under nitrogen. 4-methylpyrimidine (250 g, 2.66 mol) was added followed by Methyl 4-chlorobenzoate (453.2 g, 2.66 mol). The cooling bath was removed and the mixture was allowed to warm to room temperature and stir for 16 h. Water (3 L) and ethyl acetate (3 L) were added followed by acetic acid (200 mL). The layers were separated and the organic layer was washed with brine and dried over magnesium sulfate. The mixture was then concentrated to 800 mL and hexanes (250 mL) were added. The product was filtered, washed with hexanes, and air dried to provide a yellow solid. (388.1 g, 64%): mp 110.4–110.5° C. $^1$H NMR (acetone-d$_6$/300 MHz) 14.9 (bs, 1H), 8.8 (s, 1H), 8.4 (m, 1H), 7.7 (d, 2H, J=8.7 Hz), 7.3 (d, 2H, J=8.7 Hz), 6.9 (m, 1H), 5.9 (s, 1H).

Step 2. Preparation of dithietane compound

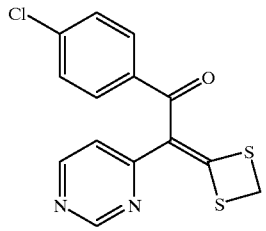

To a solution of 1-(4-chlorophenyl)-2-(4-pyrimidyl) ethanone (7.0 g, 0.03 mol) in a mixture of acetone (200 mL) and dibromomethane (75 mL) was added potassium carbonate (8.3 g, 0.06 mol), followed by the slow addition of carbon disulfide (2.6 g, 0.033 mol) over 15 minutes. The reaction mixture was stirred at room temperature for 20 h. Solvent was removed and the residue was partitioned between water and methylene chloride. The organic layer was washed with brine, dried over magnesium sulfate and filtered. The filtrate was concentrated and triturated with a mixture of ethyl acetate ether/hexane (1:5:5) to give 7.14 g of product as a yellow solid which was used without further purification in the next step.

Step 3. Preparation of 1-[5-(4-chlorophenyl)-4-(4-pyrimidinyl)-1H-pyrazol-3-yl-3,4- dimethylpiperazine

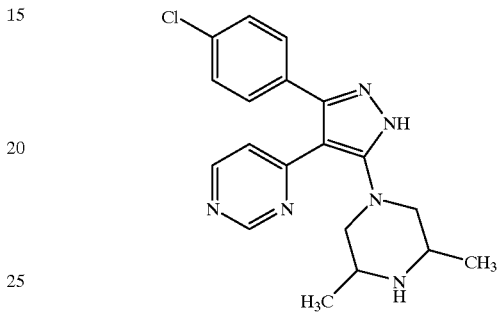

To a suspension of the crude material from Step 2 (4.0 g, 0.013 mol) in 30 mL of toluene was added a solution of 2,6-dimethylpiperazine (4.65 g, 0.04 mol) in 3 mL of acetonitrile. The reaction mixture was stirred at 85° C. for 4 h. After the removal of solvent, the crude material s as dissolved in 100 mL of dry THF and hydrazine (0.83 g, 0.026 mol) was added. The mixture was then stirred at room temperature overnight. The solvent was removed under vacuum and the residue was purified by chromatography in silica gel (ethyl acetate/methanol, 3:1 to 1:1) to afford 0.75 g of the product as a white solid (13% overall yield), mp: 212–214° C.;

Anal. Calcd. for C$_{19}$H$_{21}$ClN$_6$: C, 61.87; H, 5.74; N, 22.78. Found: C, 61.59; H, 5.28; N, 22.28.

EXAMPLE 83

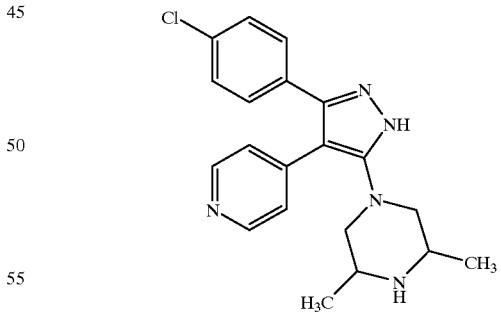

A mixture of the dithietane compound from example 2 (6.4 g, 0.02 mol) and 2,6-dimethylpiperazine (6.86 g, 0.06 mol) in 100 mL of toluene was heated at reflux for 2 h. Solvent and excess 2,6-dimethylpiperazine was removed under vacuum and the crude was used without purification. A solution of the above crude and anhydrous hydrazine (1.3 g, 0.04 mol) in 100 mL of dry THF was stirred at room temperature overnight. After the removal of THF, the residue was stirred with a mixture of ethyl acetate (100 mL) and ammonia hydroxide (20 mL) for 1 h. The precipitate was filtered and air-dried to give 3.4 g of product as a white solid (46% overall yield), mp: 236–238° C.;

Anal. Calcd. for $C_{20}H_{22}ClN_5+0.25\ H_2O$: C, 64.51; H, 6.09; N, 18.81; Cl, 9.52. Found: C, 64.28; H, 5.85; N, 18.70; Cl, 9.67.

EXAMPLE 84

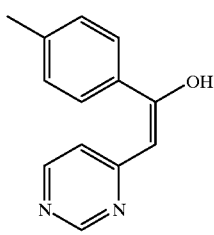

Prepared by the method described in Example 1, step 1, using 4-methylpyrimidine in place of 4-picoline. $^1$H NMR (CDCl$_3$+TFA/300 MHz) 8.96 (s, 1H), 8.10 (d, 1H), 7.88 (d, 2H), 7.36 (d, 2H), 7.09 (d, 1H), 6.43 (s, 1H), 2.48 (s, 3H). m/z 213.1003 (M+H, $C_{13}H_{12}N_2O$ requires 213.1027).

Anal. Calc'd. for $C_{13}H_{12}N_2O$: C, 73.56; H, 5.70; N, 13.20. Found: C, 73.41; H, 6.04; N, 13.17.

EXAMPLE 85

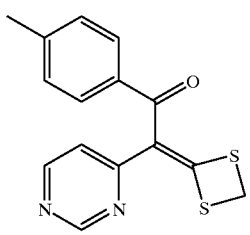

Prepared by the method described in Example 1, step 2. $^1$H NMR (CDCl$_3$/300 MHz) 9.02 (s, 1H), 8.40 (d, 1H), 7.37 (d, 2H), 7.23 (d, 2H), 6.67 (d, 1H), 4.24 (s, 2H), 2.33 (s, 3H). ESHRMS m/z 301.0488 (M+H, $C_{15}H_{12}N_2OS_2$ requires 301.0469).

Anal. Calc'd. for $C_{15}H_{12}N_2OS_2$: C, 59.97; H, 4.03; N, 9.33. Found: C, 59.43; H, 3.86; N, 9.14.

EXAMPLE 86

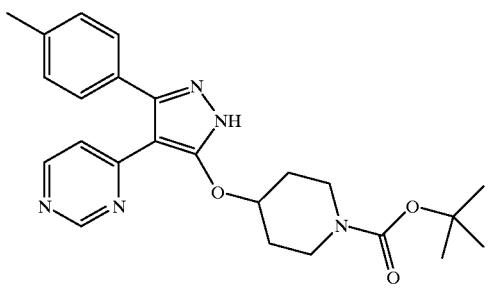

The product was prepared in an analogous manner to that of Example 32, starting with 4-hydroxy-N-t-boc piperidine and the product of Example B. $^1$H NMR (DMSO-d$_6$/300 MHz) 8.85 (s, 1H), 8.66 (d, 1H), 7.68 (d, 1H), 7.37 (d, 2H), 7.22 (d, 2H), 4.94 (m, 1H), 3.58 (m 2H), 2.34 (s, 3H), 1.97 (m, 2H), 1.69 (m, 2H), 1.40 (s, 9H). ESHRMS m/z 436.2364 (M+H, $C_{24}H_{29}N_5O_3$ requires 436.2348).

Anal. Calc'd. for $C_{24}H_{29}N_5O_3$ 0.7 $H_2O$: C, 64.33; H, 6.84; N, 15.63. Found: C, 64.40; H, 6.79; N, 15.63.

The following abbreviations have the indicated meanings:

| | | |
|---|---|---|
| Ac | = | acetyl |
| Boc | = | tertiary-butyloxycarbonyl |
| CDCl$_3$ | = | Chloroform-d |
| DMAP | = | 4-(dimethylamino)pyridine |
| DMF | = | N,N-dimethylformamide |
| DMSO | = | dimethylsulfoxide |
| EDC hydrochloride | = | 1-(3-dimethylaminopropyl)-3-ethylcarbodiimide |
| EtOAc | = | ethyl acetate |
| EtOH | = | ethanol |
| ESHRMS | = | electro-spray high resolution mass spectrum |
| ESLRMS | = | electro-spray low resolution mass spectrum |
| FABHRMS | = | fast atom bombardment high resolution mass spectrum |
| HCl | = | Hydrochloric Acid |
| H$_2$O | = | water |
| HOBt | = | 1-hydroxybenzotriazole |
| KHMDS | = | Postassium bis(trimethylsilyl)amide |
| MeOH | = | methanol |
| MgSO$_4$ | = | magnesium sulfate |
| NaCl | = | Sodium Chloride |
| NaHMDS | = | Sodium bis(trimethylsilyl)amide |
| NaOH | = | Sodium Hydroxide |
| NMR | = | nuclear magnetic resonance spectroscopy |
| TBTU | = | O-Benzotriazol-1-yl-N,N,N',N'-tetramethyluronium terafluoroborate |
| TFA | = | trifluoroacetic acid |
| THF | = | tetrahydrofuran |
| TLC | = | Thin Layer Chromatography |

From the foregoing description, one skilled in the art can easily ascertain the essential characteristics of this invention, and without departing from the spirit and scope thereof, can make various changes and modifications of the invention to adapt it to various usages and condition.

We claim:

1. The process of making compound of Formula Ia or Ib

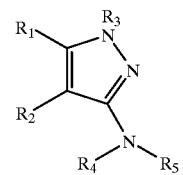

Ia

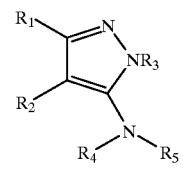

Ib wherein:

R$_1$ is selected from the group consisting of hydrogen, alkyl, O-alkyl, O-cycloalkyl, cycloalkyl, cycloalkenyl, and a 5 or 6 membered heterocycle substituted with one or more substituents selected from the group consisting of $C_{1-3}$ alkyl, halo, OH, O-alkyl, cyano, CF$_3$, OCF$_3$ and substituted phenyl wherein the substituents are selected from the group consisting of hydrogen, halo, alkoxy, alkylthio, cyano, CF$_3$, OCF$_3$, alkyl, SO$_2$CH$_3$, SO$_2$NH$_2$, SO$_2$NHCOalkyl, SO$_2$NHCOalkyl, alkenyl, and alkynyl;

R₂ is selected from the group consisting of pyridyl, pyrimidyl, triazinyl, hydrogen, halo, alkyl, and mono- or di-substituted 6-membered heterocycle wherein the substituent is selected from the group consisting of hydrogen, halo, O-alkyl, S-alkyl, cyano, CF₃, OCF₃, alkyl, alkylamino, dialkylamino, and mono or di-substituted phenyl optionally substituted from the group selected from hydrogen, halo, alkoxy, alkylthio, cyano, CF₃, OCF₃ alkyl, alkylamino, and dialkylamino;

R₃ is selected from the group selected from hydrogen, alkyl, and phenyl, wherein all but hydrogen may optionally be substituted by one or more of the group consisting of SO₂CH₃, halo, alkyl, O-alkyl, S-alkyl, cyano, CF₃, OCF₃, and SO₂NH₂;

R₄ is selected from the group consisting of alkyl, phenyl, cycloalkyl and heterocyclyl optionally substituted by one or more of the group consisting of OH, NH₂, SH, O-alkyl, NHR₇, N(R₇)₂, alkoxycarbonyl, acyl and halo;

R₅ is selected from the group consisting of alkyl, phenyl, cycloalkyl and heterocyclyl optionally substituted by one or more of the group consisting of OH, NH₂, SH, S-alkyl, O-alkyl, NHR₇, N(R₇)₂, CO₂H, halo, alkoxycarbonyl, acyl, heterocyclyl, cycloalkyl, heterocycloalkyl, and heterocyclyl;

R₄ and R₅ taken together may form a ring selected from the group consisting of morpholine, aziridine, thiomorpholine, piperidine, piperazine, and N'-piperazine;

R₇ is selected from the group consisting of alkyl and cycloalkyl;

comprising:

reacting an organometallic reagent of the formula R₂CH₂M wherein M is selected from the group consisting of Li, Na, K, and Mg, with an activated form of a carboxylic acid to produce a ketone of Formula Ic;

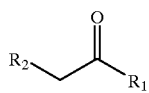

Ic treating the ketone of Formula Ic with a mixture of carbon disulfide and dihalomethane in the presence of a base and a solvent to produce the dithietane derivative of Formula Id;

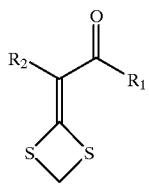

Id reacting the dithietane derivative of Formula Id with an amine of formula R₄—NH—R₅ to produce the thioamide of Formula Ie, If, or Ig;

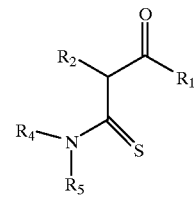

Ie

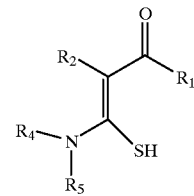

If

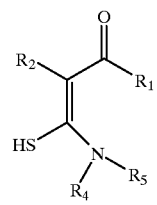

Ig condensing the thioamide of Formula Ie, If or Ig with hydrazine or substituted hydrazine.

2. The process of claim 1 wherein:

R₁ is selected from the group consisting of hydrogen, C₁₋₆ alkyl, OC₁₋₆ alkyl,)OC₃₋₆ cycloalkyl, C₃₋₇ cycloalkyl, C₃₋₇ cycloalkenyl, and 5 or 6 membered heterocycle substituted with one or more substituents selected from the group consisting of C₁₋₃ alkyl, halo, OH, OC₁₋₃ alkyl, cyano, CF₃, OCF₃ and substituted phenyl wherein the substituents are selected from one or more of the group consisting of hydrogen, halo, C₁₋₆ alkoxy, C₁₋₆ alkylthio, cyano CF₃, OCF₃, C₁₋₃ alkyl, SO₂CH₃, SO₂NH₂, SO₂NHCOC₁₋₄ alkyl, SO₂NHCOC₁₋₄ alkyl, C₁₋₄ alkenyl, and C₁₋₄ alkynyl;

R₂ is selected from the group consisting of pyridyl, pyrimidyl, triazinyl, hydrogen, halo, C₁₋₆ alkyl, and mono- or di-substituted 6-membered heterocycle wherein the substituent is selected from the group consisting of hydrogen, halo, OC₁₋₆ alkyl, SC₁₋₆ alkyl, cyano, CF₃, OCF₃, C₁₋₆ alkyl , C₁₋₆ alkylamino, C₁₋₆ dialkylamino, mono or di-substituted phenyl optionally substituted with one or more from the group selected from hydrogen, halo, C₁₋₆ alkoxy, C₁₋₆ alkylthio, cyano, CF₃, OCF₃, C₁₋₆ alkyl, C₁₋₆ alkylamino, and C₁₋₆ dialkylamino;

R₃ is selected from the group selected from hydrogen, C₁₋₆ alkyl, and phenyl wherein all by hydrogen may be optionally substituted by one or more of the group consisting of SO₂CH₃ halo, C₁₋₃ alkyl, OC₁₋₃ alkyl, SC₁₋₃ alkyl, cyano, CF₃, OCF₃, and SO₂NH₂;

R₄ is C₁₋₆ alkyl optionally substituted by one or more substituent selected from the group consisting of OH, NH₂, SH, OC₁₋₆ alkyl, NHR₇, N(R₇)₂, and halo;

R₅ is C₁₋₆ alkyl optionally substituted by one or more of the group selected from OH, NH₂, SH, SC₁₋₆ alkyl, OC₁₋₆ alkyl, NHR₇, N(R₇)₂, CO₂H, halo, 5 or 6 membered heterocyclyl, C₃₋₆ cycloalkyl, C₃₋₆ heterocycloalkyl and 5 or 6 membered heterocyclyl;

R$_4$ and R$_5$ may be taken together to form a ring selected from the group consisting of morpholine, aziridine, thiomorpholin , piperidine, piperazine and N'-C$_{1-6}$ piperazine; and R$_7$ is selected from the group consisting of C$_{1-6}$ alkyl, and C$_{3-6}$ cycloalkyl.

3. The process of claims 1 or 2 wherein the dihalomethane is dibromomethane.

4. The process of claims 1 or 2 wherein the dihalomethane is iodochloromethane.

5. The process of making a compound of Formula Ia or Ib according to claim 1 wherein the compound is selected from the group consisting of

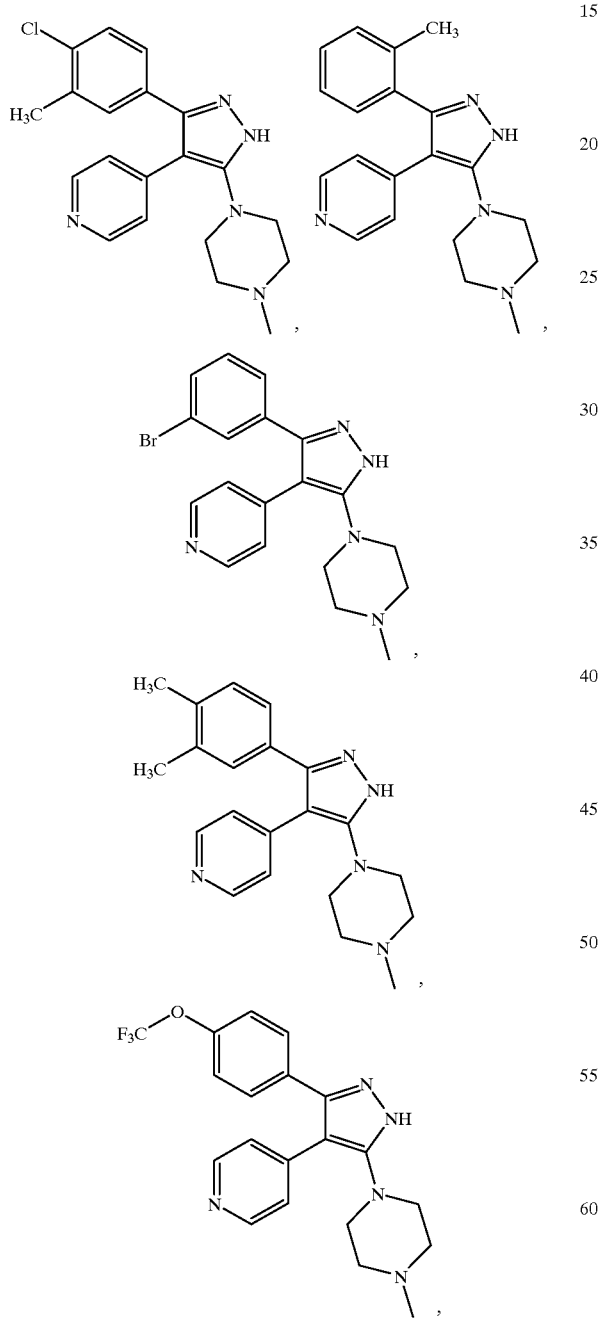
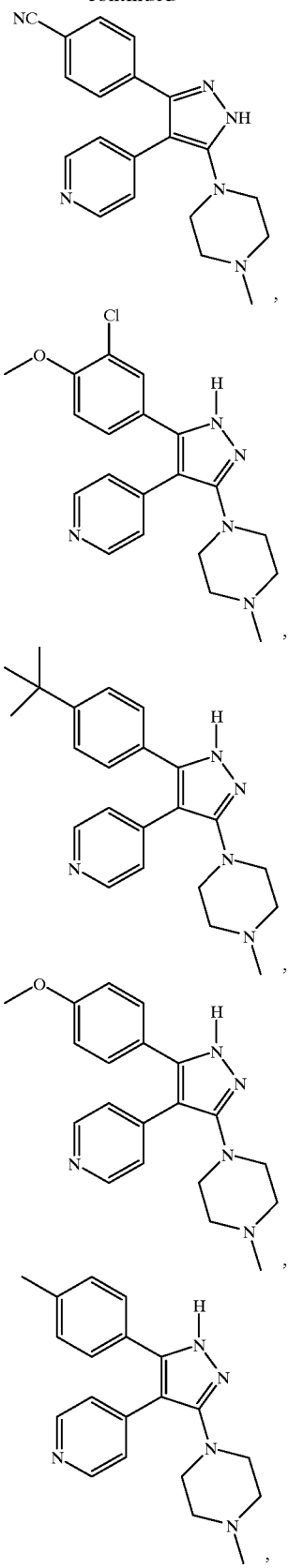

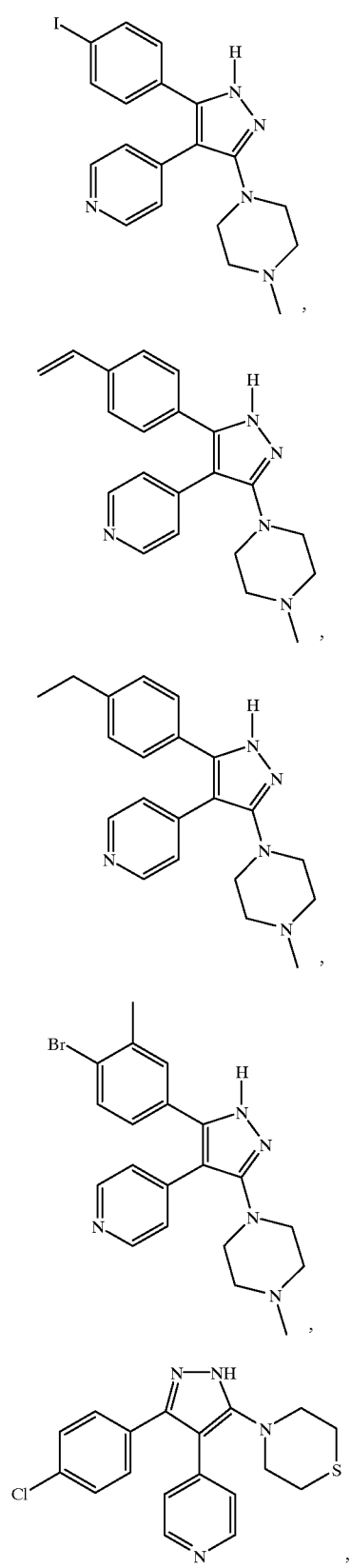
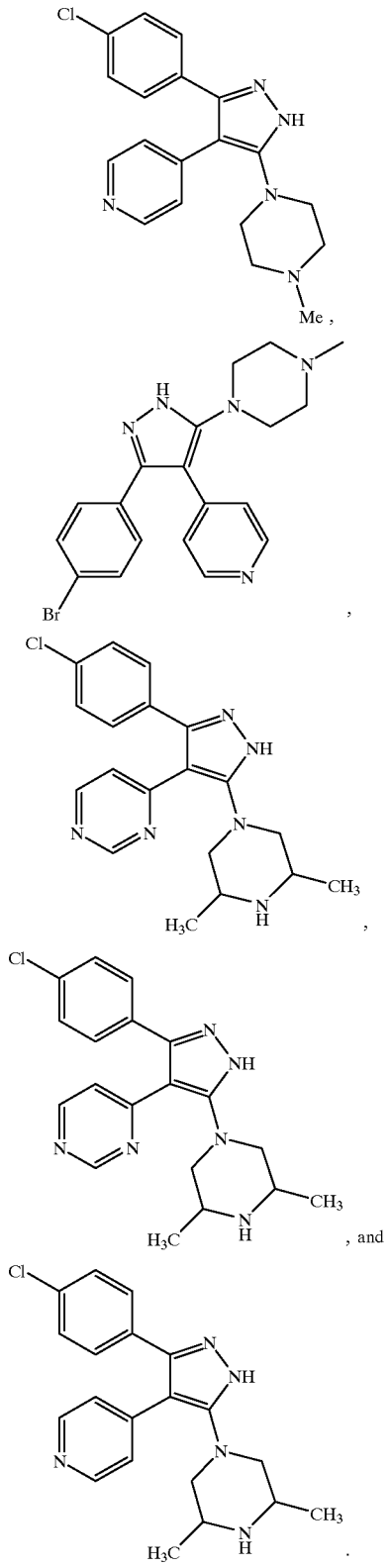
* * * * *